(12) United States Patent
Sinha et al.

(10) Patent No.: US 9,402,913 B2
(45) Date of Patent: Aug. 2, 2016

(54) CYCLOSPORINE A STEROID CONJUGATES

(71) Applicant: Allergan, Inc., Irvine, CA (US)

(72) Inventors: Santosh C. Sinha, Ladera Ranch, CA (US); Ken Chow, Newport Coast, CA (US); Liming Wang, Irvine, CA (US); Michael E. Garst, Newport Beach, CA (US); Mayssa Attar, Placentia, CA (US); Brandon D. Swift, Camarillo, CA (US)

(73) Assignee: Allergan, Inc., Irvine, CA (US)

( * ) Notice: Subject to any disclaimer, the term of this patent is extended or adjusted under 35 U.S.C. 154(b) by 80 days.

(21) Appl. No.: 14/199,432

(22) Filed: Mar. 6, 2014

(65) Prior Publication Data
US 2014/0256651 A1 Sep. 11, 2014

Related U.S. Application Data

(60) Provisional application No. 61/775,216, filed on Mar. 8, 2013.

(51) Int. Cl.
*A61K 38/12* (2006.01)
*C07K 7/64* (2006.01)
*A61K 47/48* (2006.01)
*A61K 9/00* (2006.01)

(52) U.S. Cl.
CPC ......... *A61K 47/48115* (2013.01); *A61K 9/0048* (2013.01); *A61K 47/481* (2013.01); *A61K 47/48123* (2013.01); *A61K 47/48246* (2013.01); *C07K 7/645* (2013.01)

(58) Field of Classification Search
None
See application file for complete search history.

(56) References Cited

U.S. PATENT DOCUMENTS

| | | | |
|---|---|---|---|
| 2,999,102 A | 9/1961 | Heider et al. | |
| 3,147,183 A | 9/1964 | Heider et al. | |
| 3,916,002 A | 10/1975 | Taubert et al. | |
| 4,839,342 A | 6/1989 | Kaswan | |
| 4,980,470 A | 12/1990 | Masuzawa et al. | |
| 5,474,979 A | 12/1995 | Ding et al. | |
| 5,565,568 A | 10/1996 | Cho et al. | |
| 5,688,792 A | 11/1997 | Barbachyn et al. | |
| 5,849,599 A | 12/1998 | Oh et al. | |
| 6,051,576 A | 4/2000 | Ashton et al. | |
| 6,254,860 B1 | 7/2001 | Garst | |
| 6,306,842 B1 | 10/2001 | Lai et al. | |
| 6,350,422 B1 | 2/2002 | Khare et al. | |
| 7,579,334 B2 | 8/2009 | Mercep | |
| 8,268,812 B2 | 9/2012 | Hubschwerlen et al. | |
| 8,524,671 B2 | 9/2013 | Garst et al. | |
| 8,629,111 B2 | 1/2014 | Acheampong et al. | |
| 8,633,162 B2 | 1/2014 | Acheampong et al. | |
| 8,642,556 B2 | 2/2014 | Acheampong et al. | |
| 8,648,048 B2 | 2/2014 | Acheampong et al. | |
| 8,685,930 B2 | 4/2014 | Acheampong et al. | |
| 8,716,238 B2 | 5/2014 | Garst et al. | |
| 9,175,042 B2 | 11/2015 | Garst et al. | |
| 2003/0118528 A1 | 6/2003 | Walters et al. | |
| 2005/0059583 A1 | 3/2005 | Acheampong | |
| 2006/0105941 A1 | 5/2006 | Schiffman et al. | |
| 2010/0009953 A1 | 1/2010 | Garst | |
| 2012/0088734 A1 | 4/2012 | Frydrych et al. | |
| 2012/0135939 A1 | 5/2012 | Garst et al. | |
| 2013/0324480 A1 | 12/2013 | Pettit et al. | |
| 2014/0256612 A1 | 9/2014 | Sinha et al. | |
| 2014/0256651 A1 | 9/2014 | Sinha et al. | |
| 2014/0256658 A1 | 9/2014 | Sinha et al. | |
| 2014/0256660 A1 | 9/2014 | Sinha et al. | |
| 2014/0256666 A1 | 9/2014 | Sinha et al. | |
| 2014/0256694 A1 | 9/2014 | Sinha et al. | |
| 2014/0256696 A1 | 9/2014 | Sinha et al. | |
| 2015/0065433 A1 | 3/2015 | Frydrych et al. | |

FOREIGN PATENT DOCUMENTS

| | | |
|---|---|---|
| EP | 0194972 | 9/1986 |
| EP | 0659763 A2 | 6/1995 |
| WO | 9520567 A1 | 8/1995 |
| WO | 0105819 A1 | 1/2001 |
| WO | 02087586 A1 | 11/2002 |
| WO | WO 02/087586 | * 11/2002 |
| WO | WO03031441 A1 | 4/2003 |
| WO | WO03031443 A1 | 4/2003 |
| WO | 03043657 A1 | 5/2003 |
| WO | WO03032962 A3 | 7/2003 |
| WO | 2004-082629 | 9/2004 |
| WO | 2004-112838 | 12/2004 |
| WO | 2007-008894 | 1/2007 |
| WO | 2008-069824 | 6/2008 |
| WO | 2008094507 A2 | 8/2008 |
| WO | 2009-109501 | 9/2009 |
| WO | 2012-051193 | 4/2012 |
| WO | 2012-051194 | 4/2012 |

(Continued)

OTHER PUBLICATIONS

Towler, 1990, Eye, 4, 514-520.*
Patent Cooperation Treaty, Notification of Transmittal of the International Search Report & The Written Opinion of the Int'l Searching Authority, or the Declaration, PCT/US2014/021283, Jun. 2, 2014, pp. 11.
Patent Cooperation Treaty, Notification of Transmittal of the International Search Report & The Written Opinion of the Int'l Searching Authority, or the Declaration, PCT/US2014/021283, Jun. 3, 2014, pp. 11.
Bremner, John B.; Ambrus, Joseph I.; Samosorn, Siritron, Dual action-based approaches to antibacterial agents, Current Medicinal Chemistry, 2007, 1459-1477, 14(13).

(Continued)

*Primary Examiner* — Satyanarayana R Gudibande
(74) *Attorney, Agent, or Firm* — Barbara C. Potts

(57) ABSTRACT

The present invention describes Cyclosporine A/steroid hybrid analogs. These single drug entities are formed by connecting a steroid with Cyclosporine A. Upon topical application to the eye, the conjugate hybrid would undergo enzymatic and/or hydrolytic cleavage to release the individual drugs.

2 Claims, No Drawings

(56) References Cited

FOREIGN PATENT DOCUMENTS

| WO | 2013-040441 | 3/2013 |
|---|---|---|
| WO | 2013-181339 | 12/2013 |
| WO | 2014138343 A1 | 9/2014 |
| WO | 2014138350 A1 | 9/2014 |
| WO | 2014138359 A1 | 9/2014 |
| WO | 2014138375 A1 | 9/2014 |
| WO | 2014138403 A1 | 9/2014 |
| WO | 2014138425 A1 | 9/2014 |
| WO | 2014138437 A1 | 9/2014 |

OTHER PUBLICATIONS

Cross, L.C. et al, Rules for the Nomenclature of Organic Chemistry, Section E: Stereochemistry, Pure & Appl. Chem., 1976, 11-30, 45.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
Macky, et al., Synthesis, Pharmacokinetics, Efficacy, and Rat Retinal Toxicity of a Novel Mitomycin C-Triamcinolone Acetonide Conjugate, Journal of Medicinal Chemistry,, 2002, 1122-1127, 45, American Chemical Society.
N. Das et al., Codrug: An efficient approach for drug optimization, Codrug: An efficient approach for drug optimization, 2010, 571-588, 41, European Journal of Pharmaceutical Sciences.
Philip R Hamann, An Anti-CD33 Antibody-Calicheamicin Conjugate for Treatment of Acute Myeloid Leukemia. Choice of Linker, 2002.
Pokrovskaya, Varvara; Baasov, Timor, Dual-acting hybrid antibiotics: a promising strategy to combat bacterial resistance, Expert Opinion on Drug Discovery, 2010, 883-902, 5(9).
Yang et al, An Intravitreal Sustained-Release Triamcinolone and 5-Fluorouracil Codrug in the Treatment of Experimental Proliferative Vitreoretinopathy, Arch Ophthalmology, 1998, 69-77, 116.
Yong et al, In Vitro Activities of DA-7867, a Novel Oxazolidinone, against Recent Clinical Isolates of Aerobic and Anaerobic Bacteria, Antimicrobial Agents and Chemotherapy, Jan. 2004, 352-357, vol. 48, No. 1.
Hubschwerlen et al., Design, Synthesis and Biological Evaluation of Oxazolidinone-Quinolone Hybrids, Bioorganic & Medicinal Chemistry 11, 2003, 2313-2319.
Hubschwerlen et al., Structure-Activity Relationship in the Oxazolidinone-Quinolone Hybrid Series: Influence of the Central Spacer on the Antibacterial Activity and the Mode of Action, Bioorganic & Medicinal Chemistry Letters 13, 2003, 4229-4233.
Singh et al, Mutual Prod rugs—A Recent Trend in Prodrug Design, Indian Journal of Pharmaceutical Science, 1994, 56(3), pp. 69-79.
Leppanen et al., Design and Synthesis of a Novel L-Dopa-Entacapone Codrug, Journal of Medicinal Chemistry, 2002, vol. 45, No. 6, 1379-1382.
Petersen et al., Comparative In Vitro Activities of AC98-6446, a Novel Semisynthetic Glycopeptide Derivative of the Natural Product Mannopeptimycin α, and Other Antimicrobial Agents against Gram-Positive Clinical Isolates, Antimicrobial Agents and Chemotherapy, Mar. 2004, p. 739-746, vol. 48, No. 3.
Menger et al., Synthesis and Reactivity of 5-Fluorouracil/Cytarabine Mutual Prodrugs, J. Org. Chem. 1997, 62, 9083-9088.
Vera-Cabrera et al., In Vitro Activities of New Quinolones and Oxazolidinones against Actinomadura madurae, Antimicrobial Agents and Chemotherapy, Mar. 2004, p. 1037-1039, vol. 48, No. 3.
Vera-Cabrera et al., In Vitro Activities of New Antimicrobials against Nocardia brasiliensis, Antimicrobial Agents and Chemotherapy, Feb. 2004, p. 602-604, vol. 48, No. 2.
Nudelman et al., Novel Mutual Prodrug of Retinoic and Butyric Acids with Enhanced Anticancer Activity, Journal of Medicinal Chemistry, 2000, vol. 43, No. 15, 2962-2966.
Anderegg et al., (The Quality Control Working Group) Quality Control Guidelines for MIC Susceptibility Testing of Omiganan Pentahydrochloride (MBI 226), a Novel Antimicrobial Peptide, Journal of Clinical Microbiology, Mar. 2004, p. 1386-1387, vol. 42, No. 3.
Sanchez et al., The Synthesis, Structure-Activity, and Structure-Side Effect Relationships of a Series of 8-Alkoxy- and 5-Amino-8-alkoxyquinolone Antibacterial Agents, Journal of Medicinal Chemistry, 1995, vol. 38. No. 22, 3478-4487.
Donnenfeld, Eric et al, Topical Ophthalmic Cyclosporine: Pharmacology and Clinical Uses, Survey of Ophthalmology, Jun. 2009, 321-338, 54(3).
Towler, H.M.A. et al, Combination Low Dose Cyclosporin A and Steroid Therapy in Chronic Intraocular Inflammation, Eye, Jan. 1990, 514-520, 4.
Fu, Jiping et al, Potent Nonimmunosuppressive Cyclophilin Inhibitors With Improved Pharmaceutical Properties and Decreased Transporter Inhibition, J Med Chem, 2014, 8503-8516, 57.

* cited by examiner

— 1 —

CYCLOSPORINE A STEROID CONJUGATES

RELATED APPLICATIONS

This application claims the benefit of U.S. Provisional Patent Application Ser. No. 61/775,216 filed Mar. 8, 2013, the disclosure of which is hereby incorporated in its entirety herein by reference.

FIELD OF THE INVENTION

The present invention describes Cyclosporine A/steroid hybrid analogs. These single drug entities are formed by connecting a steroid with Cyclosporine A. Upon topical application to the eye, the conjugate hybrid would undergo enzymatic and/or hydrolytic cleavage to release the individual drugs.

SUMMARY OF THE INVENTION

The steroid moiety and Cyclosporine A, of the compounds disclosed herein, are each separately connected via a covalent bond to a linker such that said compound degrades in vivo to yield the respective steroid and Cyclosporine A. Each bond is an amide bond or an ester bond depending on the nature of the compound. In other words, the single drug entity has one amide bond connecting to the steroid and/or one ester bond connecting to the Cyclosporine A.

Hybrid drugs may incorporate at least two drugs joined together by a linker moiety such as an ester, a carboxylate, a carbonyl, a carbonate, an amido, a carbamate, a ketone, an amino, an oxo, an ethylene glycol, an alkylene, a polyethylene glycol, which is cleaved enzymatically or hydrolytically in vivo to release the active drugs.

By appropriate structural design of these linkers, it may be possible to control the release of each individual drug. When the drugs are chemically combined, the resulting hybrid drug will usually have different physicochemical properties compared to the individual parent drugs, which may provide superior properties for delivery when compared to delivery of a physical mixture of the drugs. The Cyclosporine A moiety and the steroid moiety, of the compounds disclosed herein are connected each separately via a covalent bond to a linker such that said compound degrades in vivo to yield the individual Cyclosporine A and steroid.

Degradation of the ester or amide bonds generally, but not necessarily, yields the corresponding acid or alcohol by hydrolysis or a related reaction. A compound which degrades in vivo to yield the steroid and Cyclosporine A, produces the active drugs belonging to distinct classes at some point in the metabolic process of the claimed compound. In many cases, cleavage of the first amide or ester bond will release one active, and cleavage of the second amide or ester bond will release the second active.

DETAILED DESCRIPTION OF THE INVENTION

In one aspect, the present invention relates to a compound comprising a steroid and one molecule of Cyclosporine A, which are each separately connected via a covalent bond to a linker such that said compound degrades in vivo to yield the respective steroid independently and the respective Cyclosporine A drug, wherein each bond is an amide bond or an ester bond.

Applicants refer to the compounds of the invention as hybrid drugs, which have anti-inflammatory activity and are very useful compounds capable of producing the effect of an anti-inflammatory drug.

In another aspect, the present invention relates to a compound which is an active drug, which degrades in vivo into active anti-inflammatory drug(s).

The hybrid drugs of the invention provide a unique delivery of Cyclosporine A and a steroid for the treatment of ophthalmic inflammation. A single drug entity is advantageous to individual dosing of each drug because of the ability for simultaneous dosing and elimination of washout concerns when applying each drug separately.

The use of an anti-inflammatory hybrid drug is indicated where the risk of inflammation in the eye is high. The anti-inflammatory component of the composition is useful in treating inflammation associated with physical trauma to ophthalmic tissues, inflammation associated with bacterial infections and inflammation resulting from surgical procedures. The anti-inflammatory component of the composition is also useful in post-operative inflammation where there is an increased chance of bacterial infection. Other examples of ophthalmic conditions which may be treated with the compositions of the present invention include infective conditions associated with inflammation and where the use of anti-inflammatory is acceptable. Such conditions may include, but are not limited to eye infections, endophthalmitis, conjunctivitis, keratitis, blepharitis, dacryocystitis, hordeolum, corneal ulcers, anterior blepharitis, posterior blepharitis, meibomian gland dysfunction, dry eye disease, keratoconjunctivitis sicca, ocular pain, ocular pain and inflammation post-ocular surgery, bacterial conjunctivitis, anterior uveitis, post-surgical inflammation, inflammatory conditions of the palpebral, inflammatory conditions of the bulbar conjunctiva, inflammatory conditions of the cornea, inflammatory conditions of the anterior segment of the globe, allergic conjunctivitis, ocular rosacea, superficial punctate keratitis, herpes zoster keratitis, iritis, cyclitis, infective conjunctivitis, corneal injury from chemical radiation, corneal injury from thermal burns, penetration of foreign bodies, allergy, and combinations thereof.

Further, the compounds disclosed herein comprise a steroidal drug selected from: Dexamethasone, Betamethasone, Triamcinolone acetonide, Prednisolone and Hydrocortisone.

Further, the compounds disclosed herein comprise a cyclosporine A.

The present invention relates to hybrid drugs comprising a cyclosporine A moiety and one steroid moiety, or a pharmaceutical salt thereof, which are separately connected via a covalent bond to a linker such that said covalent bonds degrade in vivo to yield the respective Cyclosporine A and steroid independently.

In another aspect, the present invention relates to hybrid drugs, which degrade in vivo into a cyclosporine A and a steroidal drug.

In another aspect, the present invention relates to hybrid drugs having two bonds, wherein said bonds are asymmetrically degraded in vivo to release the two independent drugs: a cyclosporine A and a steroidal drug.

In another aspect the invention provides a method comprising administrating to an eye of a mammal a pharmaceutical composition comprising a therapeutically active amount of a hybrid drug comprising a cyclosporine A moiety and one steroid moiety, which are connected via two separate covalent bonds to a linker such that said covalent bonds degrade in vivo to yield the cyclosporine A and the steroid, wherein each bond is an ester bond or an amide bond, wherein said method is effective in the treatment of a bacterial infection or an inflammation affecting said eye.

In another aspect the invention provides a pharmaceutical composition comprising a hybrid drug comprising a cyclosporine A moiety and a steroid, which are connected via two separate covalent bonds to a linker such that said covalent bonds degrade in vivo to yield the cyclosporine A moiety and the steroid moiety, and wherein each bond is an ester bond or an amide bond, and wherein said pharmaceutical composition is formulated for topical ophthalmic administration.

Depending of the bond formation site, the cyclosporine A moiety can be linked via an ester bond and the steroid moiety can be linked via an ester bond, as shown in the following scheme:

Scheme 1

In another aspect the invention provides compounds which may comprise a linker moiety selected from, but not limited to, an ester, a carboxylate, a carbonyl, a carbonate, an amido, a carbamate, a ketone, an amino, an oxo, an ethylene glycol, a polyethylene glycol, an ethylene.

In another aspect, the invention provides compounds which may comprise a linker moiety comprising any combination of an ester, a carboxylate, a carbonyl, a carbonate, an amido, a carbamate, a ketone, an ethylene, an amino, an oxo, an ethylene glycol and/or a polyethylene glycol. Such linkers moieties and linker structures are exemplified in Table 1.

Examples of ester moieties comprised in the linkers are:

Examples of carboxylate moieties comprised in the linkers are:

Example of a carbonyl moiety comprised in the linkers is:

Example of a carbonate moiety comprised in the linkers is:

Examples of amido moieties comprised in the linkers are:

Example of carbamate moiety comprised in the linkers is:

Example of a ketone moiety comprised in the linkers is:

Examples of amino moieties comprised in the linkers are:

Example of an oxo moiety comprised in the linker is:

Example of ethylene glycol moieties comprised in the linkers are:

Example of polyethylene glycol moiety comprised in the linkers is:

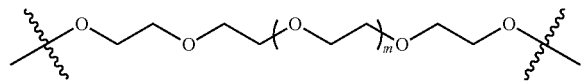

wherein "m" is 0, 1, 2, 3, 4, 5, 6, 7, 8, 9, 10, 11, 12, 13, 14, 15, 16, 17, 18, 19 or 20.

In another embodiment, the compounds disclosed herein comprise dexamethasone and cyclosporine A, such as:

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R, 4E)-1-[(11S)-5-ethyl-1,7,10,16,20,23,25,28,31-nonamethyl-11,17,26,29-tetrakis(2-methylpropyl)-3,6,9, 12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,21-dioxo-5,8,11,14,17,20-hexaoxatetracosane-1,24-dioate;

{[({(2R,4E)-1-[(11S)-5-ethyl-1,7,10,16,20,23,25,28,31-nonamethyl-11,17,26,29-tetrakis(2-methylpropyl)-3,6,9, 12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-butanedioate;

(2R,4E)-1-[(11S)-5-ethyl-1,7,10,16,20,23,25,28,31-nonamethyl-11,17,26,29-tetrakis(2-methylpropyl)-3,6,9,12,15, 18,21,24,27,30,33-undecaoxo-14,32-di(propan-2-yl)-1,4, 7,10,13,16,19,22,25,28,31-undecaazacyclotritriacontan-2-yl]-2-methylhex-4-en-1-yl 2-[(9R,10S,11S,13S,16R, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-2,2'-oxydiacetate;

1-{(2R,4E)-1-[(2S,5R,11S,14S,17R,20S,23R,26R,29S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22, 25,28,31-undecaazacyclotritriacontan-2-yl]-2-methylhex-4-en-1-yl}14-{2-[(9R,10S,11S,13S,16R, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl} rel-3-methyl-4,7,11-trioxo-8,10-dioxa-3,6-diazatetradecane-1,14-dioate;

{[({(2R,4E)-1-[(11S)-5-ethyl-1,7,10,16,20,23,25,28,31-nonamethyl-11,17,26,29-tetrakis(2-methylpropyl)-3,6,9, 12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,15-dioxo-5,8,11,14-tetraoxaoctadecane-1,18-dioate.

In another embodiment, the compounds disclosed herein comprise betamethasone and cyclosporine A, such as:

{[({(2R,4E)-1-[(11S)-5-ethyl-1,7,10,16,20,23,25,28,31-nonamethyl-11,17,26,29-tetrakis(2-methylpropyl)-3,6,9, 12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16S, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,15-dioxo-5,8,11,14-tetraoxaoctadecane-1,18-dioate;

rel-(2R)-4-({[({(2S,4E)-1-[(11R)-5-ethyl-1,7,10,16,20,23, 25,28,31-nonamethyl-11,17,26,29-tetrakis(2-methylpropyl)-3,6,9,12,15,18,21,24,27,30,33-undecaoxo-14,32-di (propan-2-yl)-1,4,7,10,13,16,19,22,25,28,31-undecaazacyclotritriacontan-2-yl]-2-methylhex-4-en-1-yl}oxy)carbonyl]methoxy)-2-[(4-{2-[(9S,10R,11R, 13R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethoxy}-4-oxobutanoyl)amino]-4-oxobutanoic acid;

{[({(2R,4E)-1-[(11S)-5-ethyl-1,7,10,16,20,23,25,28,31-nonamethyl-11,17,26,29-tetrakis(2-methylpropyl)-3,6,9, 12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16S, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-butanedioate;

{[({(2R,4E)-1-[(11S)-5-ethyl-1,7,10,16,20,23,25,28,31-nonamethyl-11,17,26,29-tetrakis(2-methylpropyl)-3,6,9, 12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16S, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,18-dioxo-5,8,11,14,17-pentaoxahenicosane-1,21-dioate;

2-[(9R,10S,11S,13S,16R,17R)-9-fluoro-11,17-dihydroxy-10,13,16-trimethyl-3-oxo-6,7,8,9,10,11,12,13,14,15,16, 17-dodecahydro-3H-cyclopenta[a]phenanthren-17-yl]-2-oxoethyl rel-(14R,16E)-13-[(2R,5R,11S,17R,29R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22, 25,28,31-undecaazacyclotritriacontan-2-yl]-14-methyl-4, 7,11-trioxo-2-(propan-2-yl)-8,10,12-trioxa-3-azaoctadec-16-en-1-oate.

In another embodiment, the compounds disclosed herein comprise triamcinolone acetonide and cyclosporine A.

In another embodiment, the compounds disclosed herein comprise prednisolone and cyclosporine A, such as:

21-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 1-({[({(2R,4E)-1-[(2S,11S,20S,26R)-5-ethyl-1,7,10,16, 20,23,25,28,31-nonamethyl-11,17,26,29-tetrakis(2-methylpropyl)-3,6,9,12,15,18,21,24,27,30,33-undecaoxo-14, 32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(3R)-3-amino-4,18-dioxo-5,8,11,14,17-pentaoxahenicosane-1,21-dioate;

6-[(6-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-6-oxohexyl)oxy]-6-oxohexyl{[({(2R,4E)-1-[(11S,17R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl(2E,5R)-6-[(11S,17R,26R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-5-methyl-8,12,19-trioxo-7,9,11,18-tetraoxatetracos-2-en-24-yl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl 6-({[({(2R,4E)-1-[(2S,11S,17R,23S,26R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-6-oxohexyl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(14R,16E)-13-[(2R,5R,11S,17R,29R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-14-methyl-4,7,11-trioxo-2-(propan-2-yl)-8,10,12-trioxa-3-azaoctadec-16-en-1-oate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(10R,18R,20E)-10-amino-17-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-18-methyl-4,11,15-trioxo-12,14,16-trioxa-5-azadocos-20-en-1-oate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-benzene-1,4-dicarboxylate;

1-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl}4-({[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(2R)-2-aminobutanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-(2E)-but-2-enedioate;

4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl}1-({[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(2S)-2-aminobutanedioate;

(2R)-2-amino-3-({[({(2R,4E)-1-[(5R,11S,26R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-3-oxopropyl 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl 1-{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}ethyl rel-4,15-dioxo-5,8,11,14-tetraoxaoctadecane-1,18-dioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-pentanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl rel-2,2'-oxydiacetate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(12R,14E)-11-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-12-methyl-5,9-dioxo-3,6,8,10-tetraoxahexadec-14-en-1-oate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,15-dioxo-5,8,11,14-tetraoxaoctadecane-1,18-dioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,18-dioxo-5,8,11,14,17-pentaoxahenicosane-1,21-dioate;

14-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl}1-{(2R,4E)-1-[(11S,23S,26S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}rel-3-methyl-4,7,11-trioxo-8,10-dioxa-3,6-diazatetradecane-1,14-dioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,21-dioxo-5,8,11,14,17,20-hexaoxatetracosane-1,24-dioate;

2-{2-[(4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-4-oxobutanoyl)oxy]ethoxy}ethyl{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate;

8-[(4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-4-oxobutanoyl)oxy]octyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate.

In another embodiment, the compounds disclosed herein comprise hydrocortisone and cyclosporine A.

Further, the compounds disclosed herein may be pro-drugs, comprising a pro-drug group either at the steroid or at the cyclosporine site.

Further, the compounds disclosed herein comprise a steroidal drug and a cyclosporine A and a pro-drug moiety selected from, but not limited to, Table 2 in any possible combination.

Further the compounds disclosed herein comprise a linker. Example of such linkers are shown in Table 1.

TABLE 1

| Linker Structure | Linker Number | | | |
|---|---|---|---|---|
| | n = 0 | n = 1 | n = 2 | n = 3 |
| (structure 1) | | L2 | | L1 |
| (structure 2) | | L3 | | |
| (structure 3) | | | L4 | |
| (structure 4) | L35 | L5 | | |

TABLE 1-continued

| Linker Structure | Linker Number | | | |
|---|---|---|---|---|
| | n = 0 | n = 1 | n = 2 | n = 3 |
| (amide linker with CH2 chain) | | | | L6 |
| (trisubstituted CH) | L7 | | | |
| (trisubstituted C with Me) | L14 | | | |
| (Me-substituted branched with CH2 chain) | | | | L15 |
| (phenyl ester linker) | | | | L16 |
| (ester linker) | | L46 | L17 | |
| (carbonate linker) | | | | L8 |
| (methylene carbonate) | L9 | | | |
| (Me-substituted carbonate) | L10 | | | |
| (Me carbonate linker with chain) | | | | L18 |
| (succinate diester linker) | | | | L11 |

TABLE 1-continued

| Linker Structure | Linker Number | | | |
|---|---|---|---|---|
| | n = 0 | n = 1 | n = 2 | n = 3 |
| | | L19 | | |
| | L12 | | | |
| | | L13 | | |
| | L20 | | | |
| | L21 | | | |
| | L22 | | | |
| | L23 | | | |
| | L24 | | | |
| | L25 | | | |
| | | L26 | | |

TABLE 1-continued

| Linker Structure | Linker Number | | | |
|---|---|---|---|---|
| | n = 0 | n = 1 | n = 2 | n = 3 |
| | L27 | | | |
| | L28 | | | |
| | L29 | | | |
| | L30 | | | |
| | L31 | | | |
| | L32 | | | |
| | L33 | | | |
| | L34 | | | |
| | L35 | | | |

TABLE 1-continued

| Linker Structure | Linker Number | | | |
|---|---|---|---|---|
| | n = 0 | n = 1 | n = 2 | n = 3 |
| (structure) | L36 | | | |
| (structure) | | L37 | | |
| (structure) | | L38 | | |
| (structure) | L39 | | | |
| (structure) | | L40 | | |
| (structure) | L41 | | | |
| (structure) | L42 | | | |
| (structure) | L43 | | | |
| (structure) | L44 | | | |

TABLE 1-continued
| Linker Structure | Linker Number | | | |
|---|---|---|---|---|
| | n = 0 | n = 1 | n = 2 | n = 3 |
| 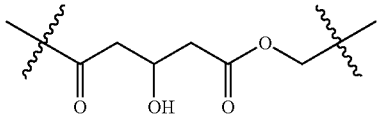 [SMILES: *COC(=O)CC(O)CC(*)=O] | L45 | | | |
| 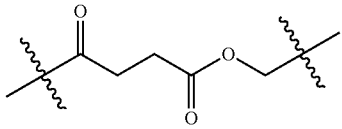 [SMILES: *COC(=O)CCC(*)=O] | L47 | | | |
| 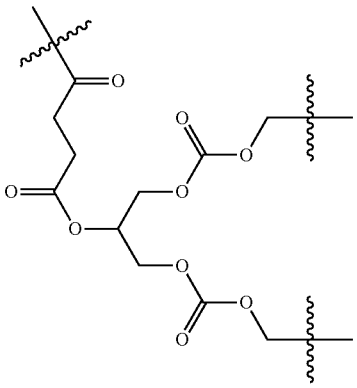 [SMILES: *COC(=O)OCC(COC(=O)OC*)OC(=O)CCC(*)=O] | L48 | | | |
| 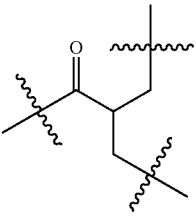 [SMILES: *CC(C*)C(*)=O] | L49 | | | |
| 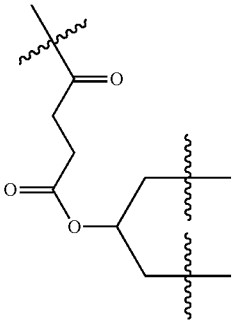 [SMILES: *CC(C*)OC(=O)CCC(*)=O] | L50 | | | |
| 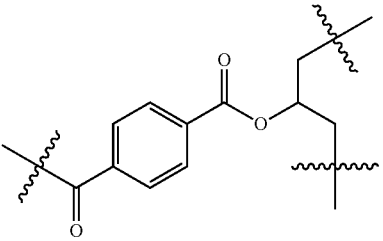 [SMILES: *CC(C*)OC(=O)c1ccc(C(*)=O)cc1] | L51 | | | |

TABLE 1-continued
| Linker Structure | Linker Number | | | |
|---|---|---|---|---|
| | n = 0 | n = 1 | n = 2 | n = 3 |
| 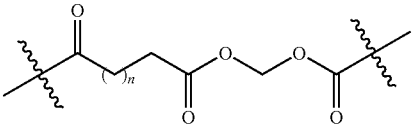 | | | L52 | L67 |
| 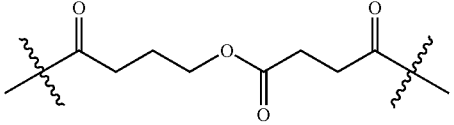 [SMILES: *C(=O)CCCOC(=O)CCC(*)=O] | | L53 | | |
| 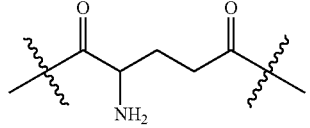 [SMILES: *C(=O)CCC(N)C(*)=O] | | L54 | | |
| 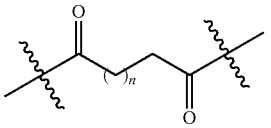 | | | | L58 |
| 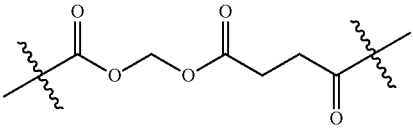 [SMILES: *C(=O)CCC(=O)OCOC(*)=O] | | L56 | | |
| 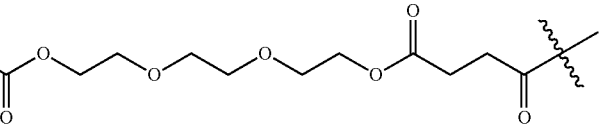 | | L57 | | |
| 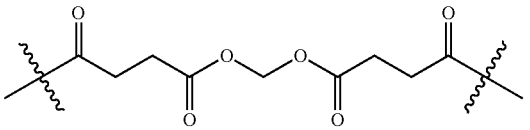 [SMILES: *C(=O)CCC(=O)OCOC(=O)CCC(*)=O] | | L59 | | |
| 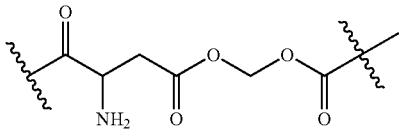 [SMILES: *C(=O)OCOC(=O)CC(N)C(*)=O] | | L60 | | |
| 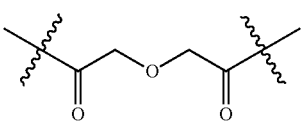 [SMILES: *C(=O)COCC(*)=O] | | L61 | | |
| 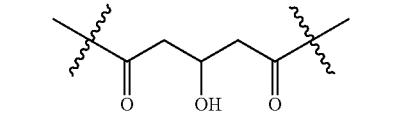 [SMILES: *C(=O)CC(O)CC(*)=O] | | L62 | | |
| 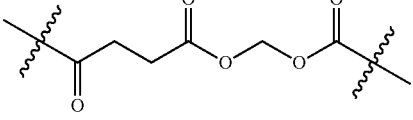 | | L63 | | |

TABLE 1-continued

| Linker Structure | Linker Number |
| --- | --- |
| | n = 0, n = 1, n = 2, n = 3 |
| (structure) | L64 |
| (structure) | L65 |
| (structure) | L66 |
| (structure) | L68 |
| (structure) | L69 |
| (structure) | L70 |
| (structure) | L71 |
| (structure) | L72 |
| (structure) | L73 |
| (structure) | L74 |

TABLE 1-continued

| Linker Structure | Linker Number | | | |
|---|---|---|---|---|
| | n = 0 | n = 1 | n = 2 | n = 3 |
| (L75 structure) | L75 | | | |
| (L76 structure) | L76 | | | |
| (L77 structure) | L77 | L115 | L116 | |
| (L78 structure) | L78 | | | |
| (L79 structure) | L79 | | | |
| (L80 structure) | L80 | | | |
| (L81 structure) | L81 | | | |
| (L82 structure) | L82 | | | |
| (L83 structure) | L83 | | | |
| (L84 structure) | L84 | | | |

TABLE 1-continued

| Linker Structure | Linker Number | | | |
|---|---|---|---|---|
| | n = 0 | n = 1 | n = 2 | n = 3 |
| (structure) | L85 | | | |
| (structure) | L86 | | | |
| (structure) | L87 | L88 | | |
| (structure) | L89 | | | |
| (structure) | L90 | | | |
| (structure) | L91 | | | |
| (structure) | L92 | | | |
| (structure) | L93 | | | |

TABLE 1-continued

| Linker Structure | Linker Number |
|---|---|
| (L94 structure) | L94 |
| (L95 structure) | L95 |
| (L96 structure) | L96 |
| (L97 structure) | L97 |
| (L98 structure) | L98 |

TABLE 1-continued

| Linker Structure | Linker Number | | | |
|---|---|---|---|---|
| | n = 0 | n = 1 | n = 2 | n = 3 |
| (structure) | L99 | | | |
| (structure) | L100 | L101 | L102 | |
| (structure) | | | | L103 |
| (structure) | L104 | | | |
| (structure) | L105 | | | |
| (structure) | L106 | | | |
| (structure) | L107 | | | |
| (structure) | L108 | | | |

TABLE 1-continued
| Linker Structure | Linker Number |
| --- | --- |
| | n = 0    n = 1    n = 2    n = 3 |
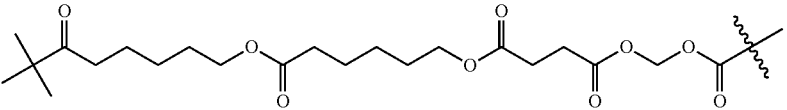 [SMILES: *C(=O)OCOC(=O)CCC(=O)OCCCCCC(=O)OCCCCCC(=O)C(C)(C)C]
L109
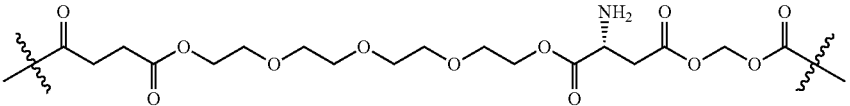 [SMILES: *C(=O)CCC(=O)OCCOCCOCCOCCOC(=O)[C@H](N)CC(=O)OCOC(*)=O]
L110
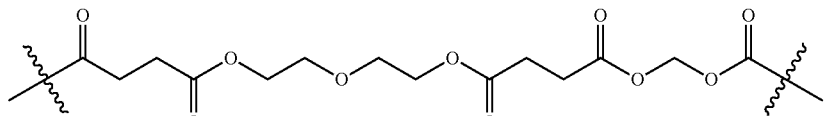
L111
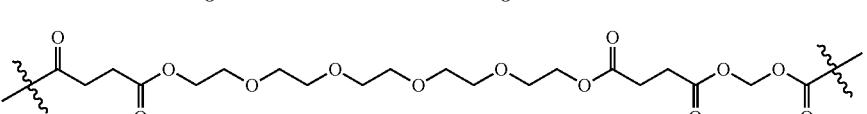
L112
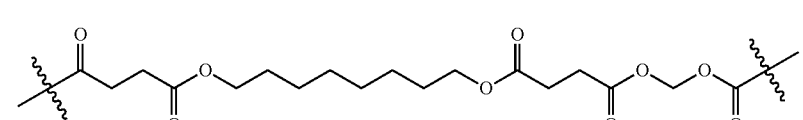
L113
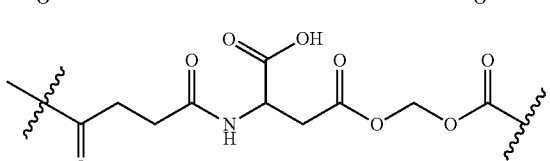
L114
Further the compounds disclosed herein may comprise a pro-drug moiety selected from Table 2:
TABLE 2
| Pro-drug Structure | Pro-drug Number |
| --- | --- |
| 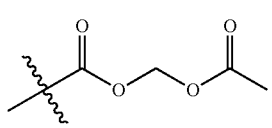 [SMILES: *C(=O)OCOC(C)=O] | P1 |
| 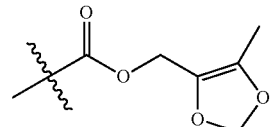 | P2 |
| 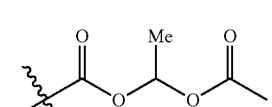 | P3 |
TABLE 2-continued
| Pro-drug Structure | Pro-drug Number |
| --- | --- |
| 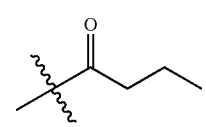 | P4 |
| 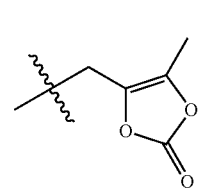 [SMILES: *Cc1oc(=O)oc1C] | P5 |
| 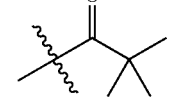 | P6 |
| 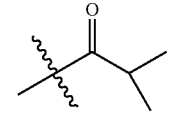 [SMILES: *C(=O)C(C)C] | P7 |

TABLE 2-continued

| Pro-drug Structure | Pro-drug Number |
|---|---|
| (pivaloyl / tert-butyl ketone) | P8 |
| (phenyl ketone, isobutyryl) | P9 |
| (tert-butyl ester) | P10 |
| (valine ketone, NH2) | P11 |
| (aspartic acid derivative, H2N, OH) | P12 |
| (val-val dipeptide ketone) | P13 |
| (glutamic acid carbonate methyl ester) | P14 |
| (val-val carbonate methyl ester) | P15 |

Compounds of the invention are shown in Table 3.

TABLE 3

| Compound number | IUPAC Names |
|---|---|
| 19 | 21-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 1-({[({(2R,4E)-1-[(2S,11S,20S,26R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(3R)-3-amino-4,18-dioxo-5,8,11,14,17-pentaoxahenicosane-1,21-dioate |
| 18 | 6-[(6-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-6-oxohexyl)oxy]-6-oxohexyl {[({(2R,4E)-1-[(11S,17R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate |
| 23 | 8-[(4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-4-oxobutanoyl)oxy]octyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate |
| 17 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl (2E,5R)-6-[(11S,17R,26R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-5-methyl-8,12,19-trioxo-7,9,11,18-tetraoxatetracos-2-en-24-yl rel-butanedioate |
| 16 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl 6-({[({(2R,4E)-1-[(2S,11S,17R,23S,26R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-6-oxohexyl rel-butanedioate |
| 27 | 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-(14R,16E)-13-[(2R,5R,11S,17R,29R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-14-methyl-4,7,11-trioxo-2-(propan-2-yl)-8,10,12-trioxa-3-azaoctadec-16-en-1-oate |
| 15 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(14R,16E)-13-[(2R,5R,11S,17R,29R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-14-methyl-4,7,11-trioxo-2-(propan-2-yl)-8,10,12-trioxa-3-azaoctadec-16-en-1-oate |
| 22 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,21-dioxo-5,8,11,14,17,20-hexaoxatetracosane-1,24-dioate |
| 21 | 2-{2-[(4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-4-oxobutanoyl)oxy]ethoxy}ethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate |

TABLE 3-continued

| Compound number | IUPAC Names |
|---|---|
| 28 | {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,15-dioxo-5,8,11,14-tetraoxaoctadecane-1,18-dioate |
| 26 | rel-(2R)-4-({[({(2S,4E)-1-[(11R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-2-[(4-{2-[(9S,10R,11R,13R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethoxy}-4-oxobutanoyl)amino]-4-oxobutanoic acid |
| 14 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(10R,18R,20E)-10-amino-17-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-18-methyl-4,11,15-trioxo-12,14,16-trioxa-5-azadocos-20-en-1-oate |
| 13 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-benzene-1,4-dicarboxylate |
| 12 | 1-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 4-({[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(2R)-2-aminobutanedioate |
| 11 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-(2E)-but-2-enedioate |
| 25 | {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,18-dioxo-5,8,11,14,17-pentaoxahenicosane-1,21-dioate |
| 20 | {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,18-dioxo-5,8,11,14,17-pentaoxahenicosane-1,21-dioate |
| 32 | {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,15-dioxo-5,8,11,14-tetraoxaoctadecane-1,18-dioate |
| 10 | 4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 1-({[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(2S)-2-aminobutanedioate |
| 9 | (2R)-2-amino-3-({[({(2R,4E)-1-[(5R,11S,26R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-3-oxopropyl 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-butanedioate |
| 8 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl 1-{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}ethyl rel-4,15-dioxo-5,8,11,14-tetraoxaoctadecane-1,18-dioate |
| 31 | 1-{(2R,4E)-1-[(2S,5R,11S,14S,17R,20S,23R,26R,29S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl} 14-{2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl} rel-3-methyl-4,7,11-trioxo-8,10-dioxa-3,6-diazatetradecane-1,14-dioate |
| 7 | 14-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 1-{(2R,4E)-1-[(11S,23S,26S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl} rel-3-methyl-4,7,11-trioxo-8,10-dioxa-3,6-diazatetradecane-1,14-dioate |
| 6 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,18-dioxo-5,8,11,14,17-pentaoxahenicosane-1,21-dioate |
| 5 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,15-dioxo-5,8,11,14-tetraoxaoctadecane-1,18-dioate |
| 30 | (2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-2,2'-oxydiacetate |

TABLE 3-continued

| Compound number | IUPAC Names |
|---|---|
| 4 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(12R,14E)-11-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-12-methyl-5,9-dioxo-3,6,8,10-tetraoxahexadec-14-en-1-oate |
| 29 | {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-butanedioate |
| 24 | {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16S,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-butanedioate |
| 3 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-pentanedioate |
| 2 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate |
| 1 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl (2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl rel-2,2'-oxydiacetate |

Some compounds of the invention have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of the invention are able to form.

The acid addition salt form of a compound of the invention that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic acid and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of the invention that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of the invention and their salts can be in the form of a solvate, which is included within the scope of the present invention. Such solvates include for example hydrates, alcoholates and the like.

In still another embodiment of the invention, there are provided methods for treating or preventing eye conditions such as: conjunctivitis, keratitis, blepharitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis, in a patient suffering thereof. Such methods can be performed, for example, by administering to a subject in need thereof a therapeutically effective amount of at least one compound of the invention, or any combination thereof, or pharmaceutically acceptable salts, hydrates, solvates, crystal forms thereof.

The present invention concerns the use of a compound of the invention or a pharmaceutically acceptable salt thereof, for the manufacture of a medicament fir the treatment of conjunctivitis, keratitis, blepharitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

The compounds of the invention may also be administered as pharmaceutical compositions in a form suitable for topical use, for example, as oily suspensions, as solutions or suspensions in aqueous liquids or nonaqueous liquids, or as oil-in-water or water-in-oil liquid emulsions.

Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate.

A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |

-continued

| Ingredient | Amount (% w/v) |
|---|---|
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan. The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 μl.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions such as conjunctivitis, keratitis, blepharitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis, post-surgical inflammation, inflammatory conditions of the palpebral and bulbar conjunctiva, cornea, and anterior segment of the globe, such as allergic conjunctivitis, ocular rosacea, dry eye, blepharitis, meibomian gland dysfunction, superficial punctate keratitis, herpes zoster keratitis, iritis, cyclitis, selected infective conjunctivitis, corneal injury from chemical radiation, or thermal burns, penetration of foreign bodies, allergy, and combinations thereof.

Thus, in further embodiments of the invention, there are provided methods for treating conjunctivitis, keratitis, blepharitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis, post-surgical inflammation, inflammatory conditions of the palpebral and bulbar conjunctiva, cornea, and anterior segment of the globe, such as allergic conjunctivitis, ocular rosacea, dry eye, blepharitis, meibomian gland dysfunction, superficial punctate keratitis, herpes zoster keratitis, iritis, cyclitis, selected infective conjunctivitis, corneal injury from chemical radiation, or thermal burns, penetration of foreign bodies, allergy, and combinations thereof.

Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

It is to be understood that both the foregoing general description and the following detailed description are exemplary and explanatory only and are not restrictive of the invention claimed. As used herein, the use of the singular includes the plural unless specifically stated otherwise.

The following abbreviations are used in the general schemes and in the examples:

Boc tert-Butyloxycarbonyl

EDCI 1-Ethyl-3-(3-dimethylaminopropyl)carbodiimide

Boc$_2$O di-tert-butyl dicarbonate

THF tetrahydrofuran

NaOH sodium hydroxide

DMAP 4-dimethylaminopyridine

CH$_2$Cl$_2$ dichloromethane

HCl hydrochloric acid

M molar

NaHCO$_3$ sodium bicarbonate

CHCl3 chloroform

EtOH ethanol

DMF N,N-dimethylformamide

MeOH methanol

NaOAc sodium acetate

FA fumaric acid

PG protecting group

General Synthesis

In Scheme 1A the synthesis of hybrid analogs were started with the steroid. EDCI coupling with a linker gave a steroid linker ester, which was converted to the cesium salt with cesium carbonate. This salt reacted with iodo CyA prepared according to WO2008/069824 A2 and yielded the desired hybrid compound. It should be noted that the brief description on each of the arrows for each conversion has been added for illustration purpose sonly and should not be regarded as limiting with respect to the sequence of each individual step.

Scheme 1A

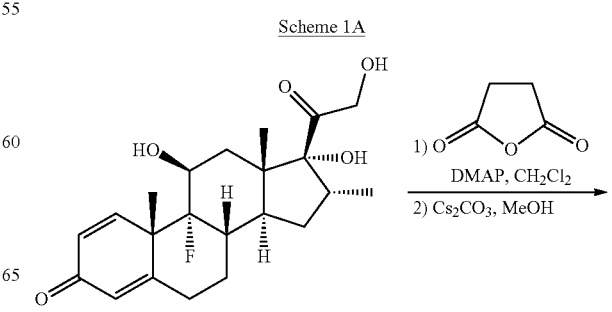

45
-continued
46
-continued
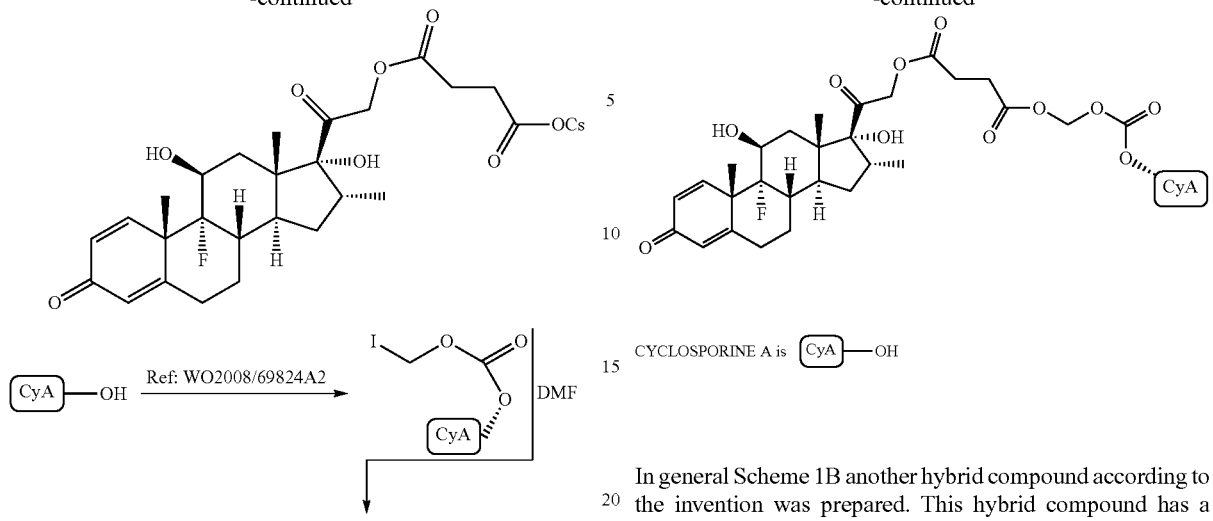
CYCLOSPORINE A is [CyA]—OH
In general Scheme 1B another hybrid compound according to the invention was prepared. This hybrid compound has a polyethylene/keto type of linker.
Scheme 1B
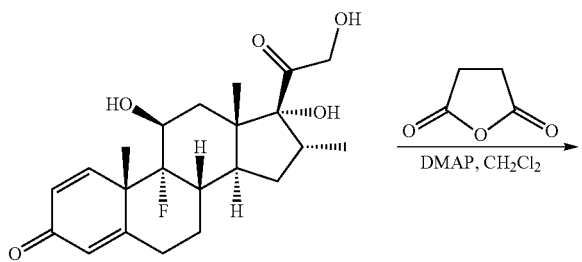
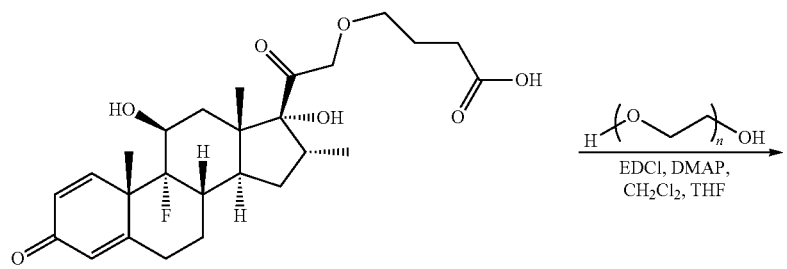
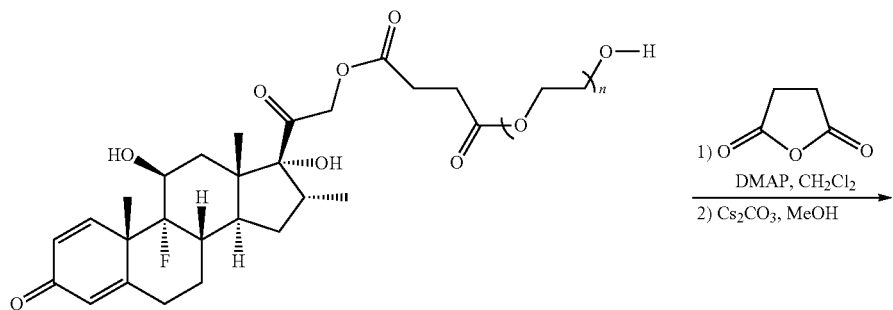

-continued

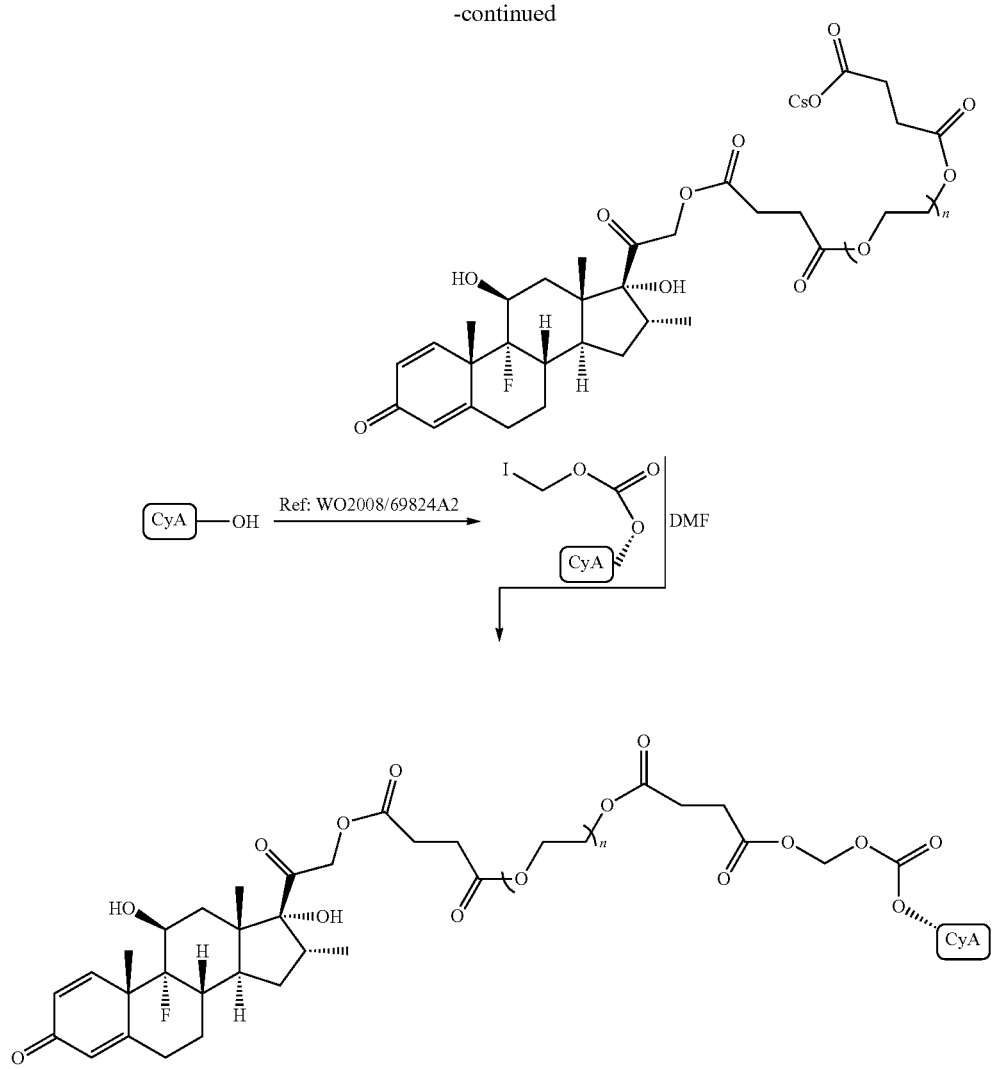

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of hydrogen $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACDLabs version 12.5 or ChemBioDraw Ultra version 12.0.2.

In general, characterization of the compounds is performed according to the following methods. Proton nuclear magnetic resonance (¹H NMR) and carbon nuclear magnetic resonance (¹³C NMR) spectra were recorded on a Varian 300 or 600 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity). The mass spectrometry data were determined on a Shimadzu LCMS-IT-TOF instrument.

The Cyclosporine A molecule can be also represented by either structures:

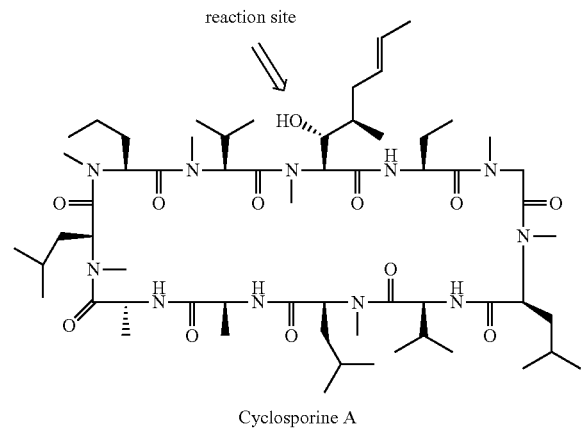

Cyclosporine A

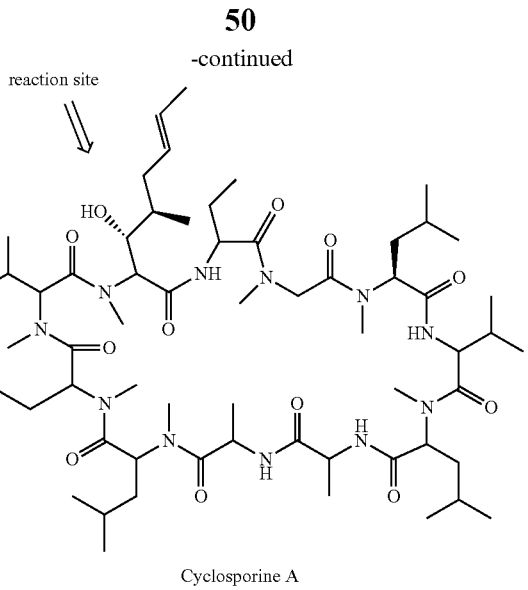

Cyclosporine A

The formation of the hybrid compounds was checked by ¹H-NMR, comparing the chemical shifts of the protons from the CH₂ group identified in the schemes shown below, and identified as "$H^a$", "$H^b$", "$CH_2{}^c$" for the starting material and as "$H^{a*}$", "$H^{b*}$", "$CH_2{}^{c*}$" or "$c*$" for of the corresponding protons on the newly formed hybrid molecule wherein "*" indicates the hybrid compound. Applicants have indicated with arrows the location of these protons and the reaction site of the pro-drug moiety, where available. Each scheme shows the formation of the new hybrid drug. Each table describes the results for the new hybrid drug and the linker number and the pro-drug number, where existing. The linker and pro-drug moiety numbers are as described in Table 1 and 2 respectively.

Examples of Compounds of the Invention

Prednisolone reacted with one molecule of Cyclosporine A to form the following hybrid compounds as shown in Scheme 2 with the results described in Table 4.

Scheme 2

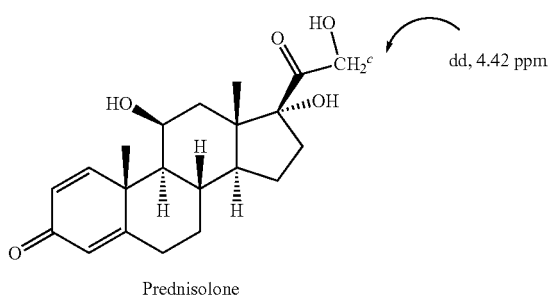

dd, 4.42 ppm

Prednisolone

-continued
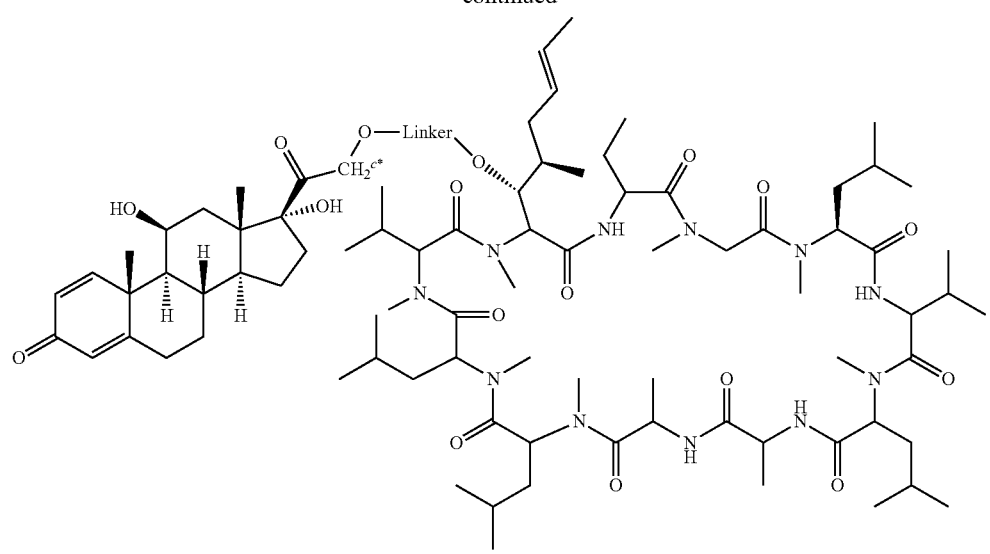
TABLE 4
| Comp. Linker | Structure | CH$_2^{c*}$ δ (ppm) | Mass |
|---|---|---|---|
| 1 L61 | 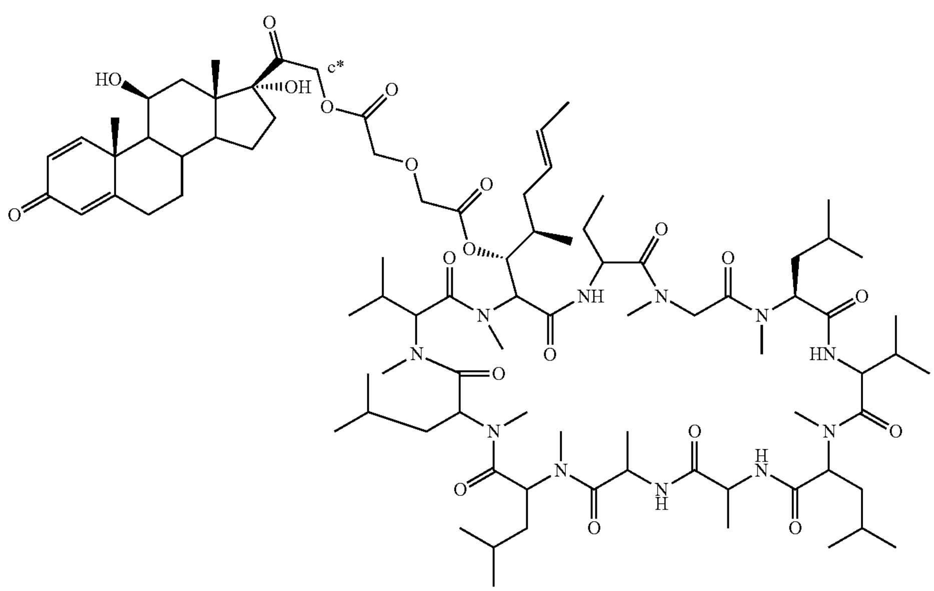 [SMILES: C/C=C/C[C@@H](C)[C@@H](OC(=O)COCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 4.99 (dd) | 1683 MNa$^+$ |

TABLE 4-continued
| | | | | |
|---|---|---|---|---|
| 2 L63 | | 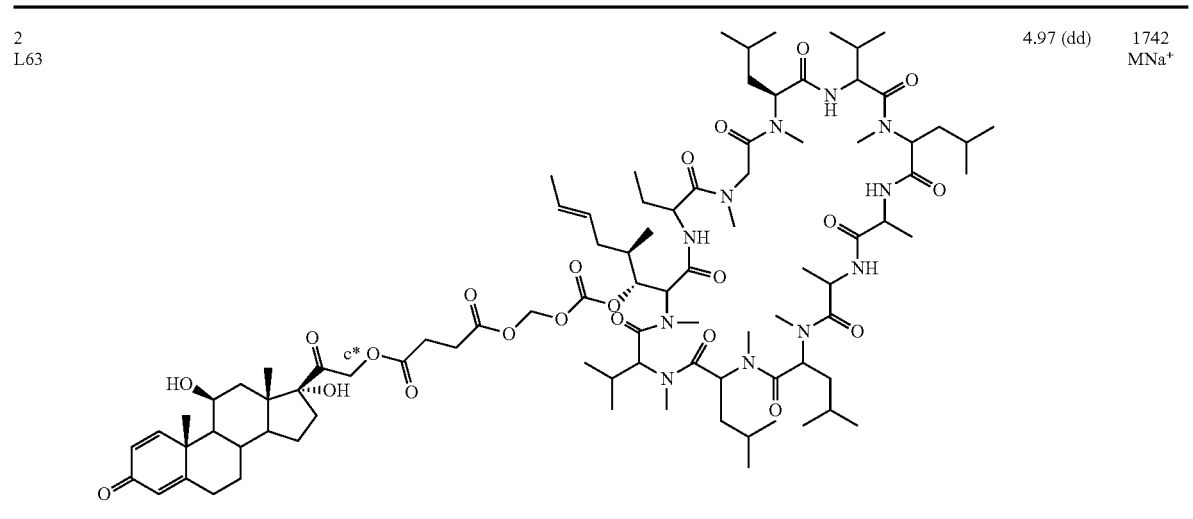 | 4.97 (dd) | 1742 MNa+ |
*Comp.
| Linker | Structure | Ha* | Hb* | Mass |
|---|---|---|---|---|
| 2 L63 | 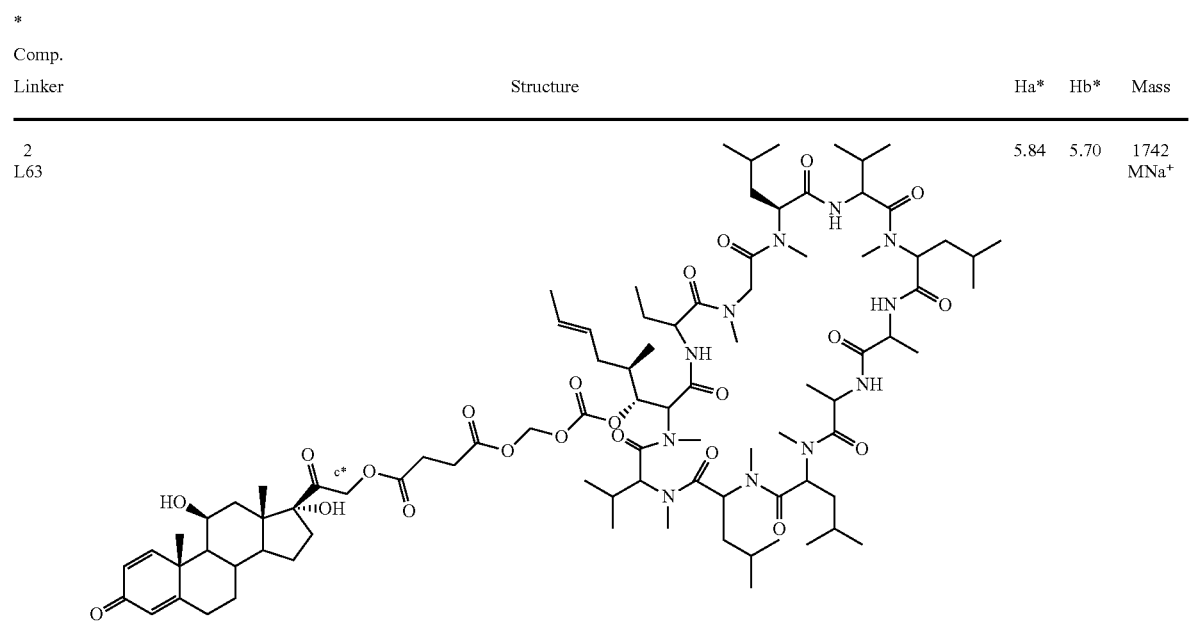 | 5.84 | 5.70 | 1742 MNa+ |

TABLE 4-continued
| L67 3 | 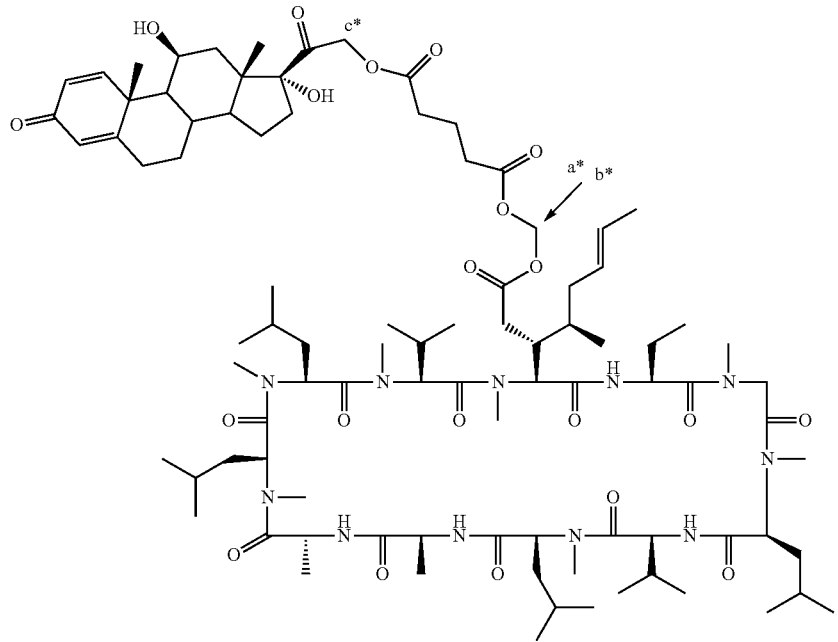 [SMILES: C/C=C/C[C@@H](C)[C@@H](CC(=O)OCOC(=O)CCCC(=O)OCC(=O)[C@@]1(O)CCC2C3CCC4=CC(=O)C=C[C@]4(C)C3[C@@H](O)C[C@@]21C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | 5.79 | 5.70 | 1756 MNa+ |
| L41 4 | 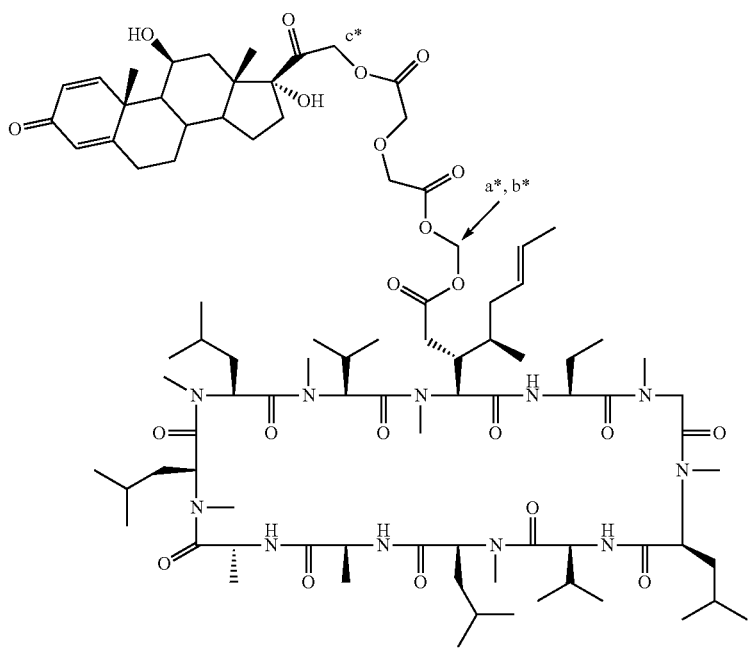 [SMILES: C/C=C/C[C@@H](C)[C@@H](CC(=O)OCOC(=O)COCC(=O)OCC(=O)[C@@]1(O)CCC2C3CCC4=CC(=O)C=C[C@]4(C)C3[C@@H](O)C[C@@]21C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | 5.85 | 5.79 | 1759 MNa+ |

TABLE 4-continued
| | | | | |
|---|---|---|---|---|
| L68 5 | 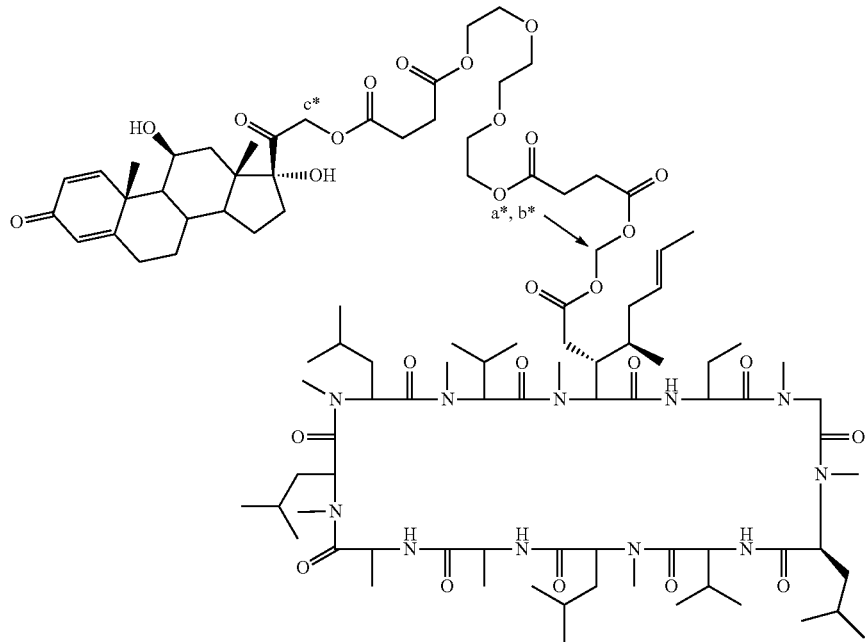 [SMILES: C/C=C/C[C@@H](C)[C@@H](CC(=O)OCOC(=O)CCC(=O)OCCOCCOCCOC(=O)CCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.87 | 5.70 | 1974 MNa+ |
| L69 6 | 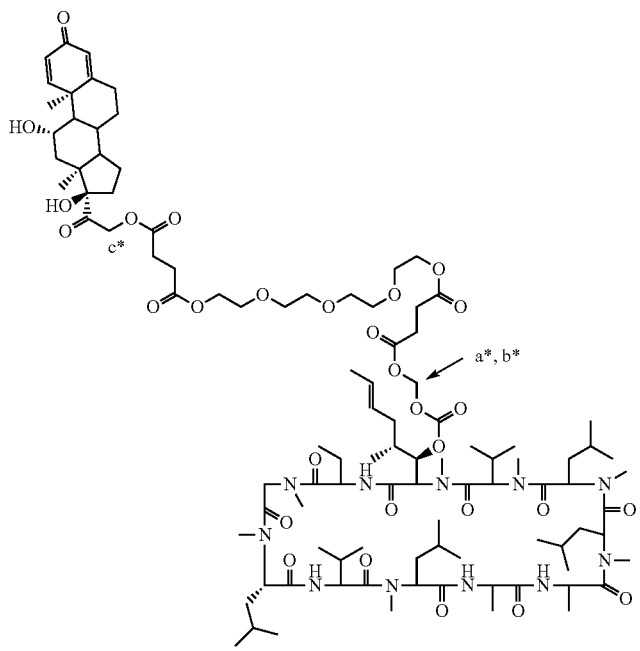 [SMILES: C/C=C/C[C@@H](C)[C@@H](OC(=O)OCOC(=O)CCC(=O)OCCOCCOCCOCCOC(=O)CCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.82 | 5.89 | 2018 MNa+ |

TABLE 4-continued
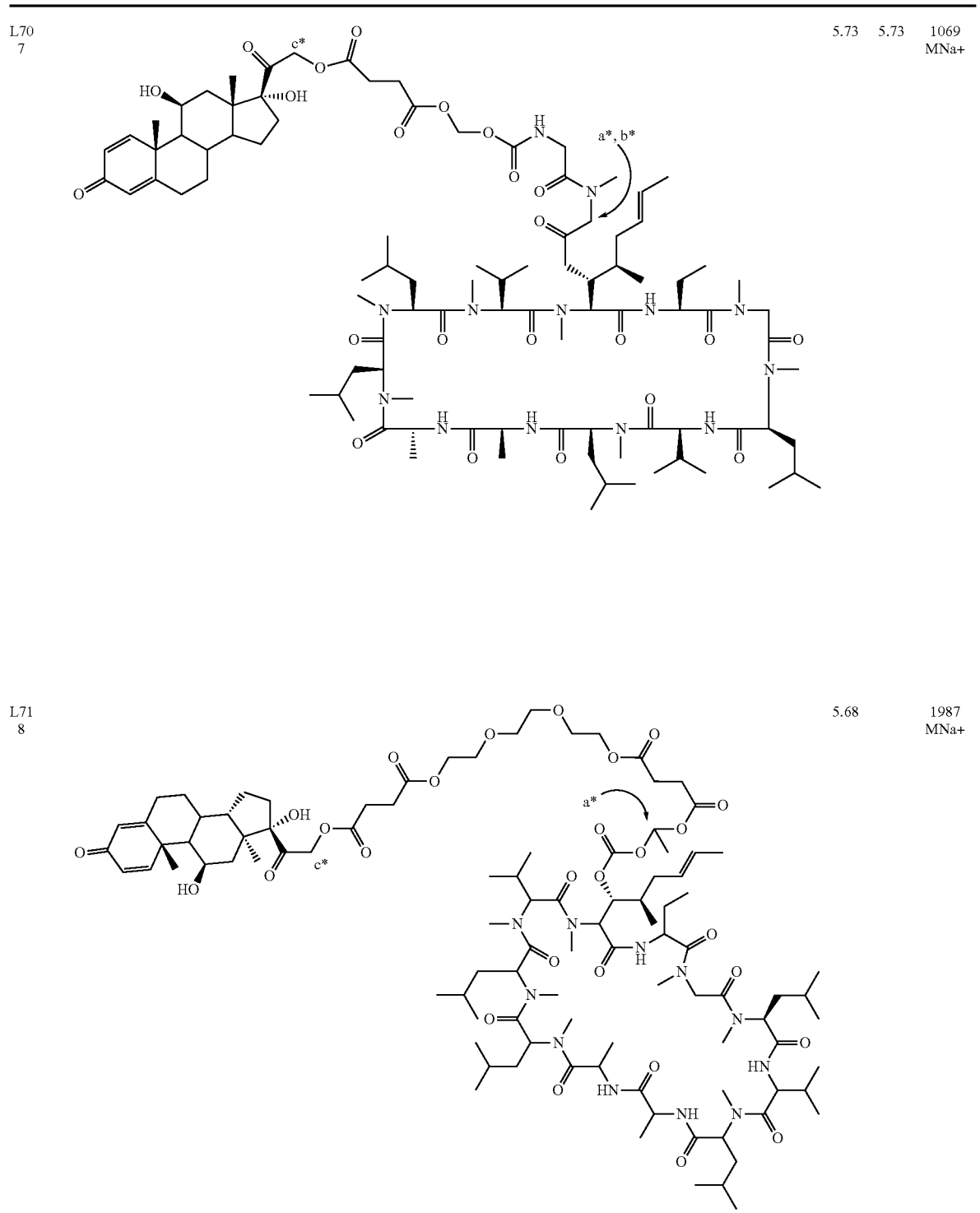
| | | | |
|---|---|---|---|
| L70 7 | | 5.73 5.73 | 1069 MNa+ |
| L71 8 | | 5.68 | 1987 MNa+ |

TABLE 4-continued
| | | | |
|---|---|---|---|
| L72 9 | 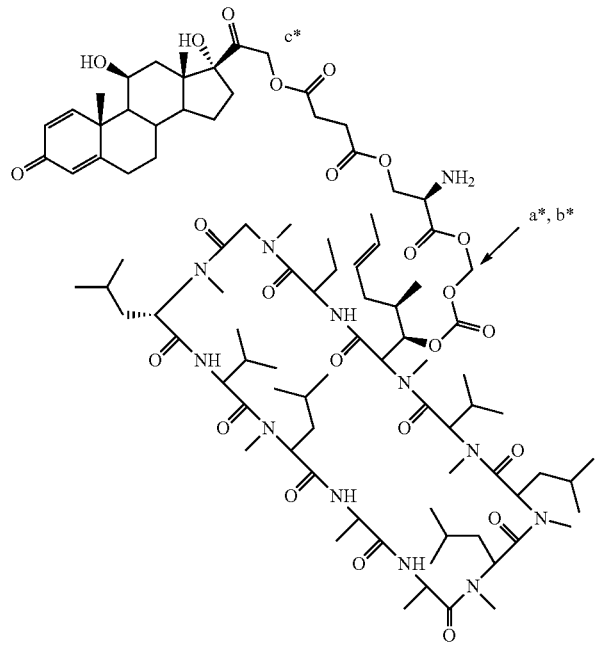 [SMILES: C/C=C/C[C@@H](C)[C@@H](OC(=O)OCOC(=O)[C@H](N)COC(=O)CCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.67 | 1806 MNa+ |
| L73 10 | 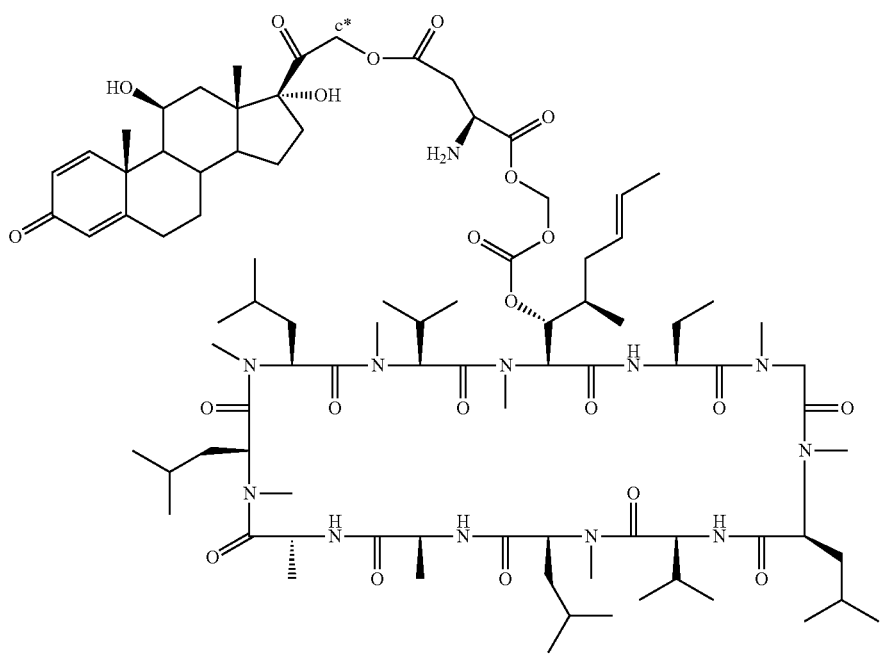 [SMILES: C/C=C/C[C@@H](C)[C@@H](OC(=O)OCOC(=O)[C@@H](N)CC(=O)OCC(=O)[C@@]1(O)CCC2C3CCC4=CC(=O)C=C[C@]4(C)C3[C@@H](O)C[C@@]21C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | 5.65 | |

TABLE 4-continued
| | | | | |
|---|---|---|---|---|
| L74 11 | 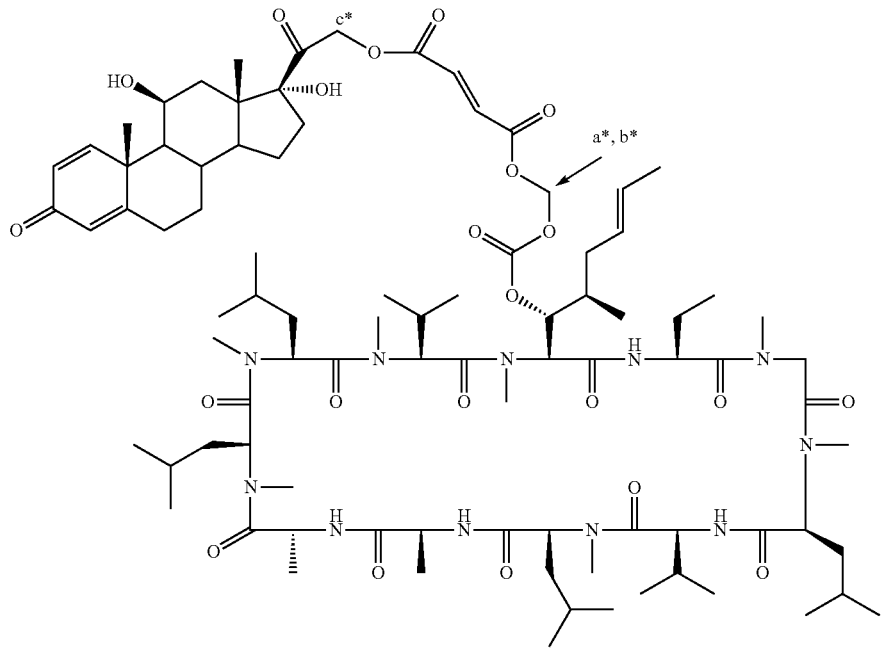 [SMILES: C/C=C/C[C@@H](C)[C@@H](OC(=O)OCOC(=O)/C=C/C(=O)OCC(=O)[C@@]1(O)CCC2C3CCC4=CC(=O)C=C[C@]4(C)C3[C@@H](O)C[C@@]21C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | 5.94 | 5.80 | 1739 MNa+ |
| 12 L60 | 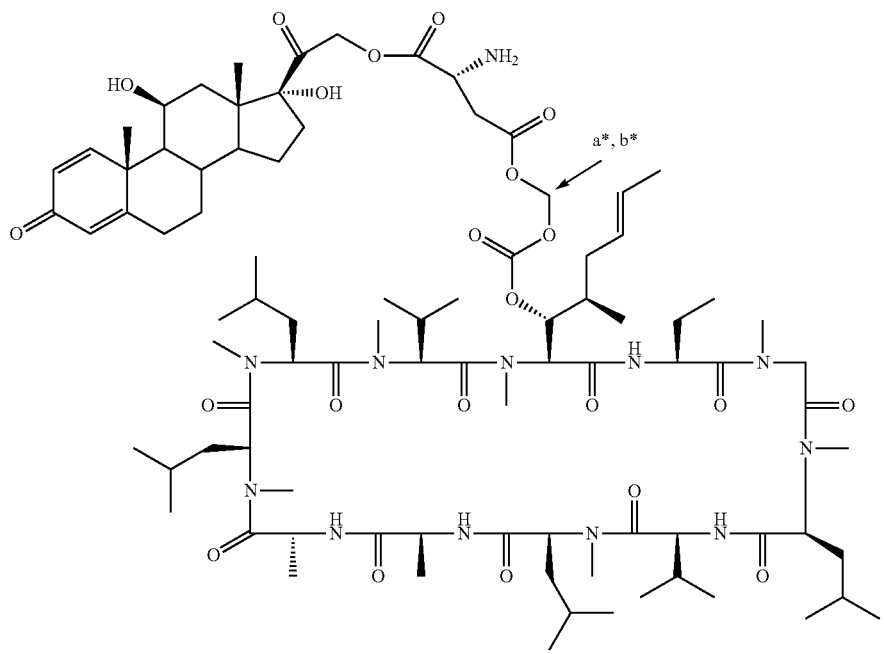 [SMILES: C/C=C/C[C@@H](C)[C@@H](OC(=O)OCOC(=O)C[C@@H](N)C(=O)OCC(=O)[C@@]1(O)CCC2C3CCC4=CC(=O)C=C[C@]4(C)C3[C@@H](O)C[C@@]21C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | 5.94 | 5.80 | 1739 MNa+ |

TABLE 4-continued
| 13 L99 | 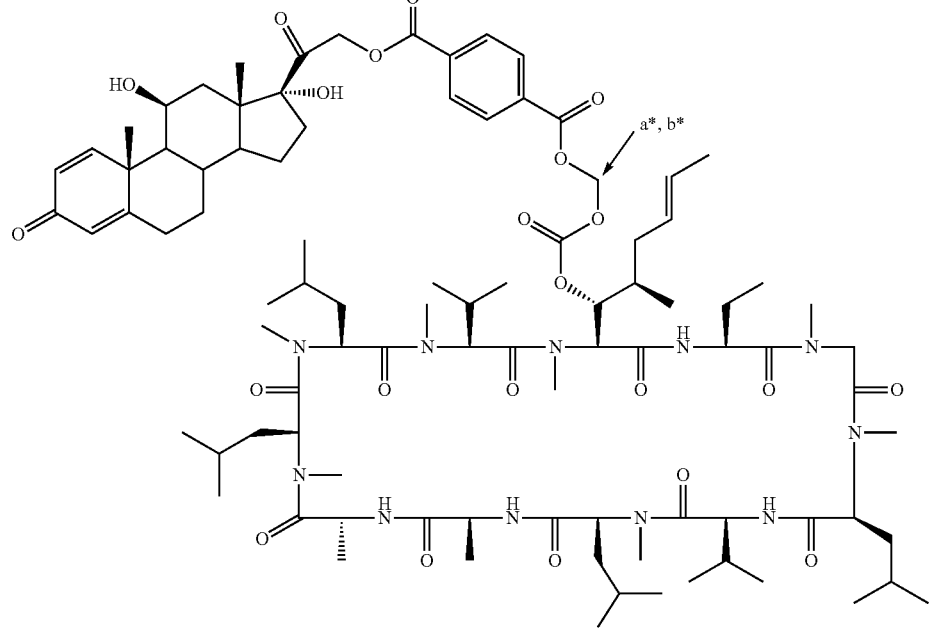 | 6.03 | 5.98 | 1789 MNa+ |
| 14 L105 | 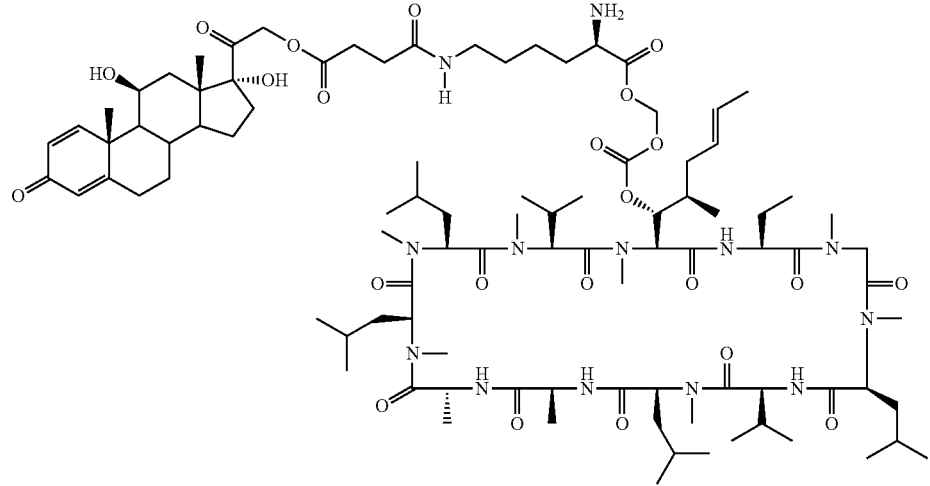 [SMILES: C/C=C/C[C@@H](C)[C@@H](OC(=O)OCOC(=O)[C@H](N)CCCCNC(=O)CCC(=O)OCC(=O)[C@@]1(O)CCC2C3CCC4=CC(=O)C=C[C@]4(C)C3[C@@H](O)C[C@@]21C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | | 5.83 | 1870 MNa+ |
| 15 L106 | 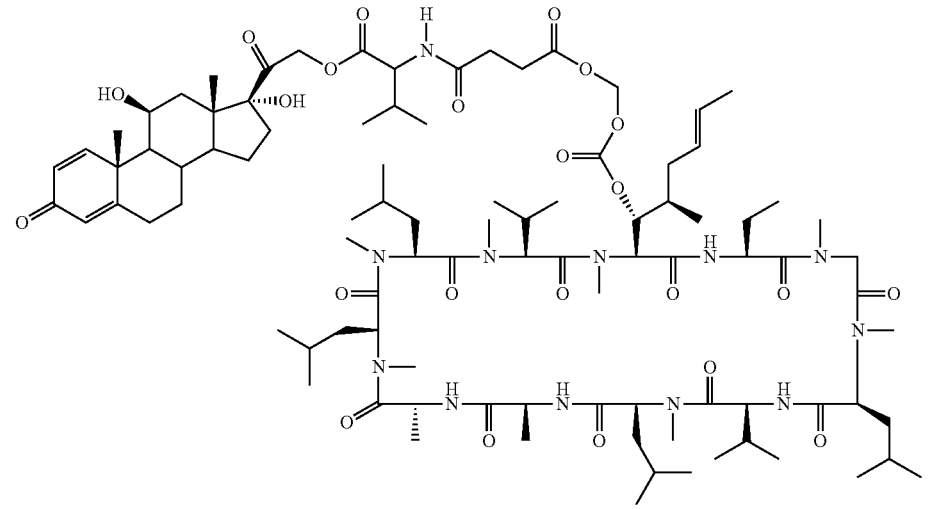 [SMILES: C/C=C/C[C@@H](C)[C@@H](OC(=O)OCOC(=O)CCC(=O)NC(C(=O)OCC(=O)[C@@]1(O)CCC2C3CCC4=CC(=O)C=C[C@]4(C)C3[C@@H](O)C[C@@]21C)C(C)C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | 5.77 | 5.72 | 1840 MNa+ |

TABLE 4-continued
| 16 L107 | 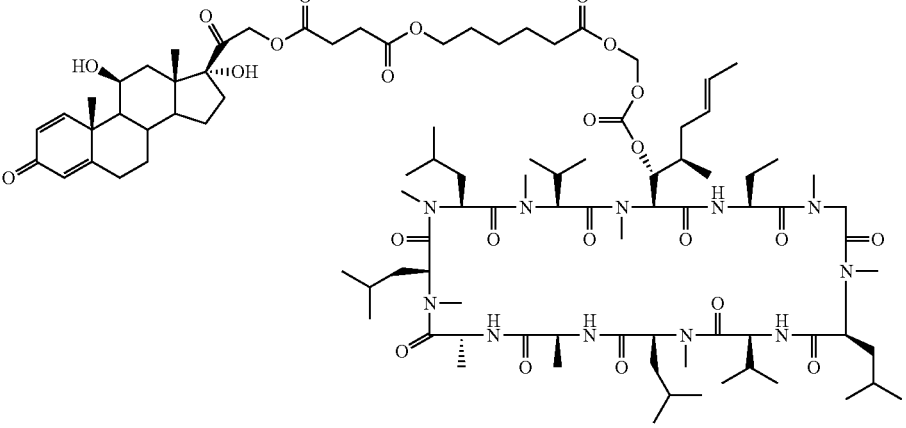 | 5.80 | 5.66 | 1855 MNa+ |
| 17 L108 | 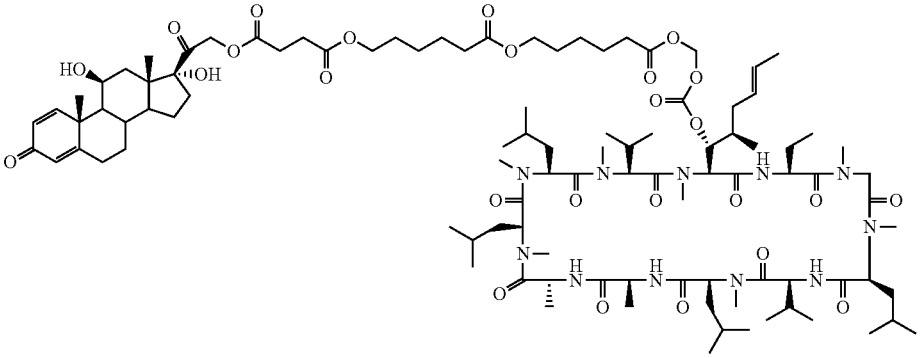 [SMILES: C/C=C/C[C@@H](C)[C@@H](OC(=O)OCOC(=O)CCCCCOC(=O)CCCCCOC(=O)CCC(=O)OCC(=O)[C@@]1(O)CCC2C3CCC4=CC(=O)C=C[C@]4(C)C3[C@@H](O)C[C@@]21C)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C] | 5.81 | 5.66 | 1969 MNa+ |
| 18 L109 | 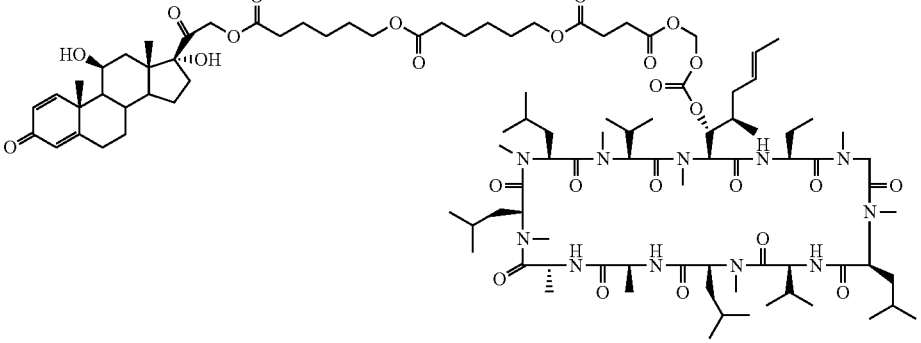 | 5.81 | 5.68 | 1969 MNa+ |

TABLE 4-continued
| 19 L110 | 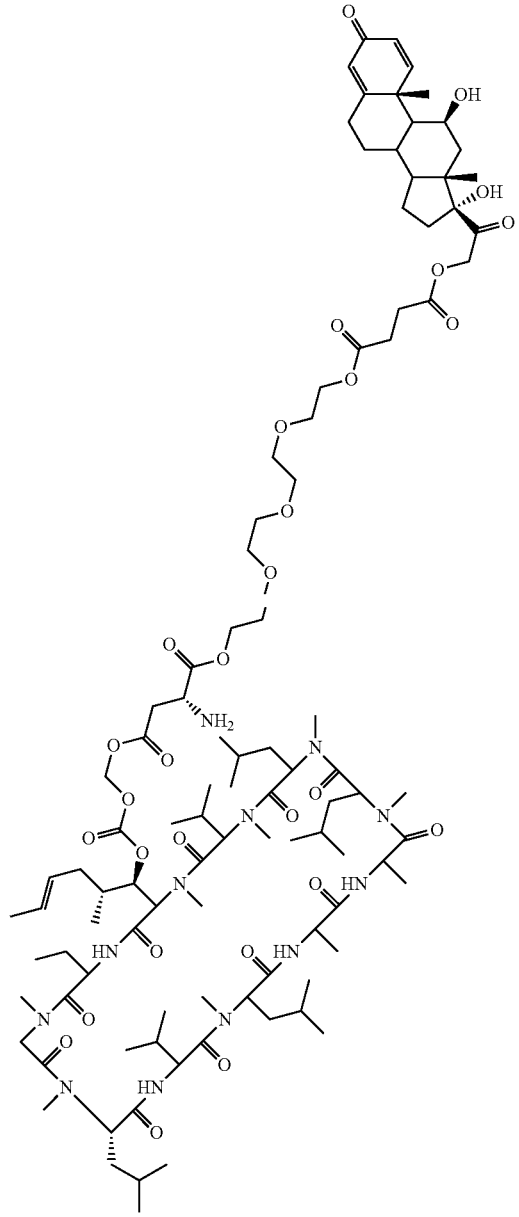 [SMILES: C/C=C/C[C@@H](C)[C@@H](OC(=O)OCOC(=O)C[C@@H](N)C(=O)OCCOCCOCCOCCOC(=O)CCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.85 | 5.67 | 2031 MNa+ |

TABLE 4-continued
| | | | | |
|---|---|---|---|---|
| 21 L111 | 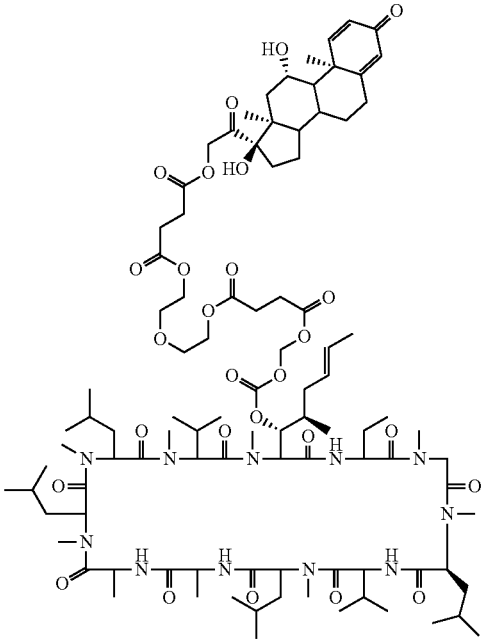 [SMILES: C/C=C/C[C@@H](C)[C@@H](OC(=O)OCOC(=O)CCC(=O)OCCOCCOC(=O)CCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.81 | 5.69 | 1929 MNa+ |
| 22 L112 | 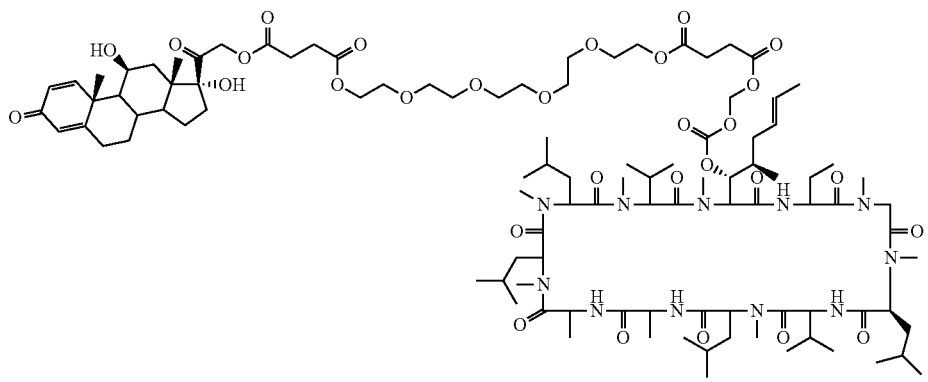 [SMILES: C/C=C/C[C@@H](C)[C@@H](OC(=O)OCOC(=O)CCC(=O)OCCOCCOCCOCCOCCOC(=O)CCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.82 | 5.69 | 2061 MNa+ |
| 23 L113 | 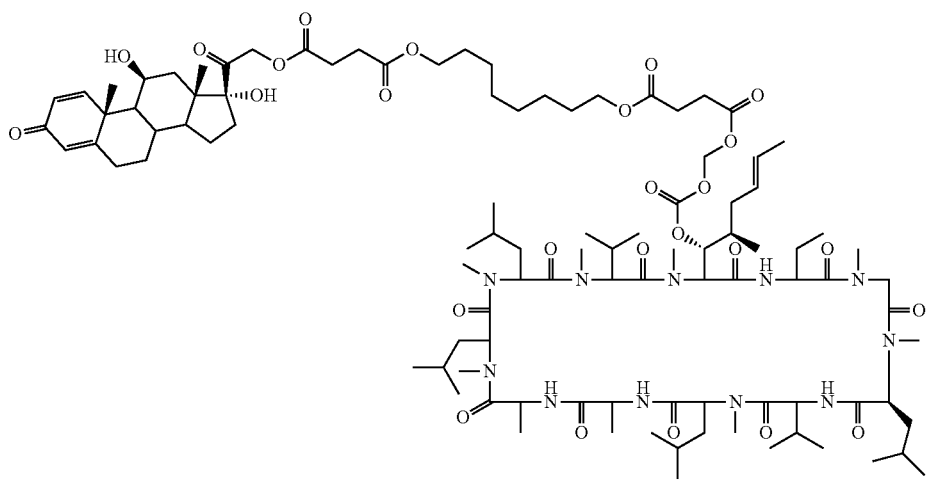 [SMILES: C/C=C/C[C@@H](C)[C@@H](OC(=O)OCOC(=O)CCC(=O)OCCCCCCCCOC(=O)CCC(=O)OCC(=O)[C@@]1(O)CCC2C3CCC4=CC(=O)C=C[C@]4(C)C3[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.82 | 5.69 | 1970 MNa+ |

Betamethasone reacted with one molecule of Cyclosporine A to form the following hybrid compounds as shown in Scheme 3 with the results described in Table 5.
Scheme 3
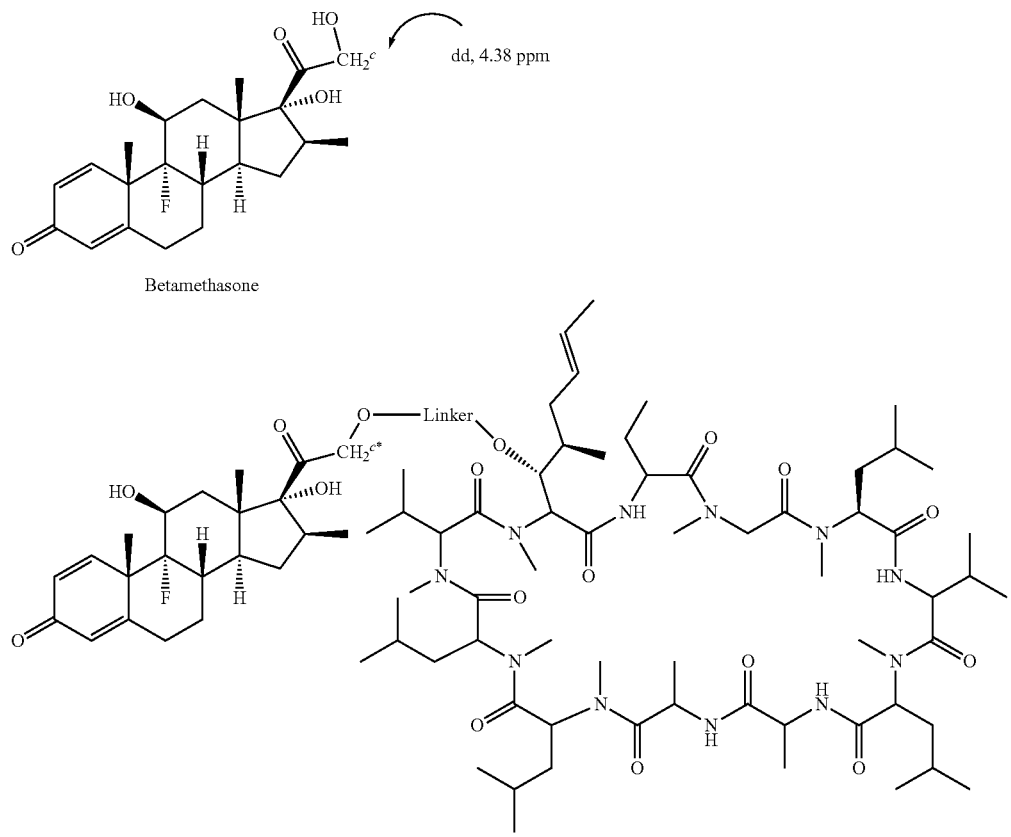
TABLE 5
| * Comp. Linker | Structure | Ha* δ (ppm) | Hb* δ (ppm) | Mass |
|---|---|---|---|---|
| 24 L63 | 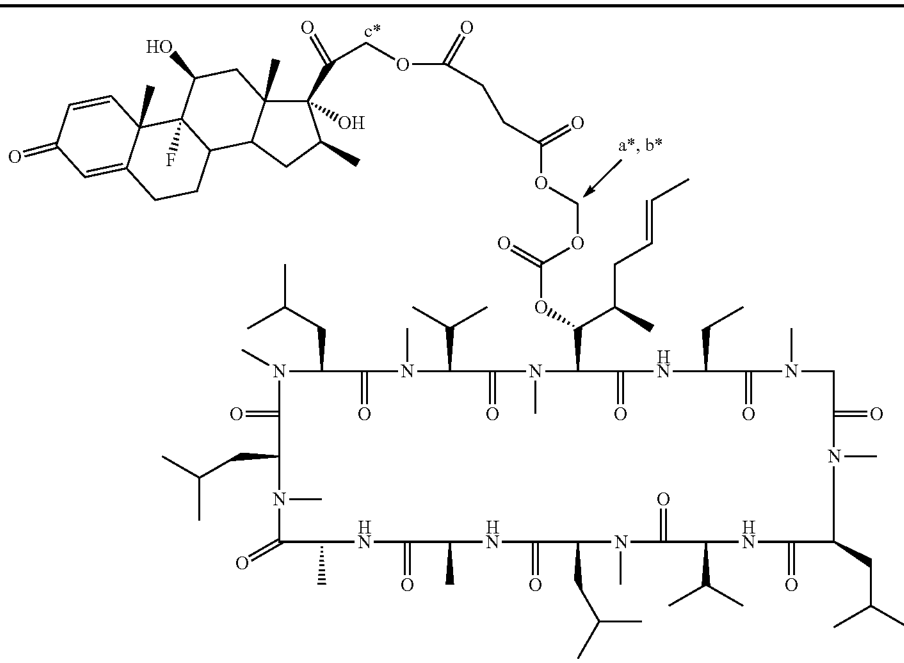 | 5.93 | 5.61 | 1773 MNa+ |

| * Comp. Linker | Structure | Ha* δ (ppm) | Hb* δ (ppm) | Mass |
|---|---|---|---|---|
| 25 L69 | 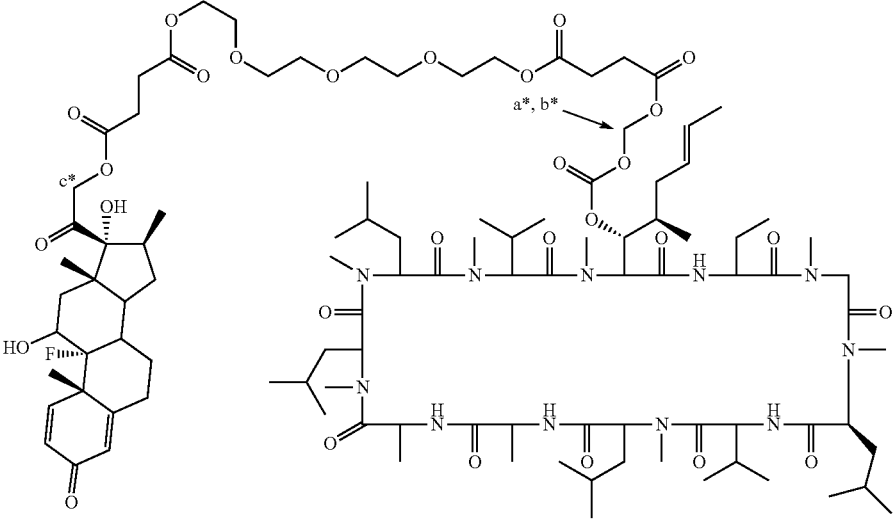 [SMILES: C/C=C/C[C@@H](C)[C@@H](OC(=O)OCOC(=O)CCC(=O)OCCOCCOCCOCCOC(=O)CCC(=O)OCC(=O)[C@@]1(O)[C@@H](C)CC2C3CCC4=CC(=O)C=C[C@]4(C)[C@@]3(F)C(O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.81 | 5.69 | 2050 MNa+ |
| 26 L114 | 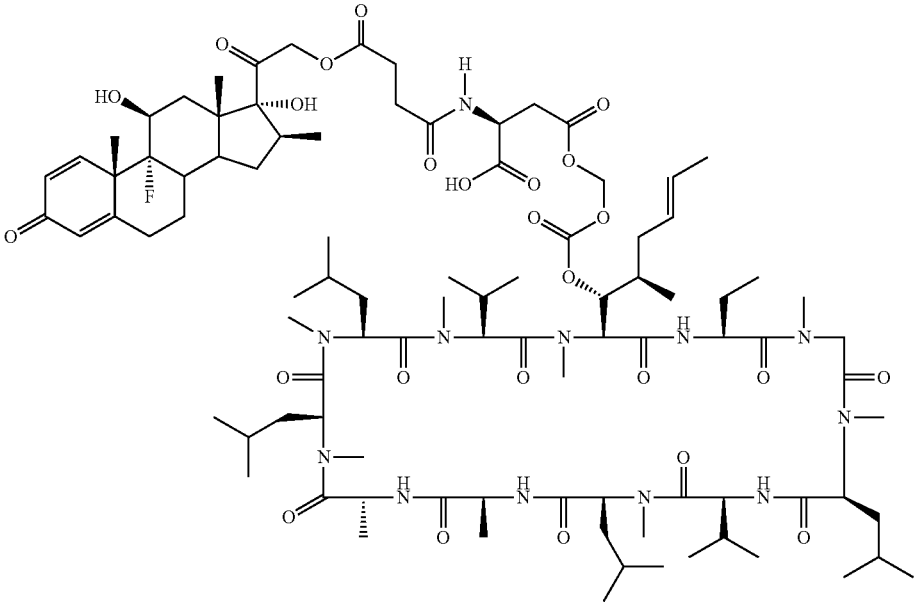 | 5.62 | 5.50 | 1889 MNa+ |

TABLE 5-continued
| * Comp. Linker | Structure | Ha* δ (ppm) | Hb* δ (ppm) | Mass |
|---|---|---|---|---|
| 27 L106 | 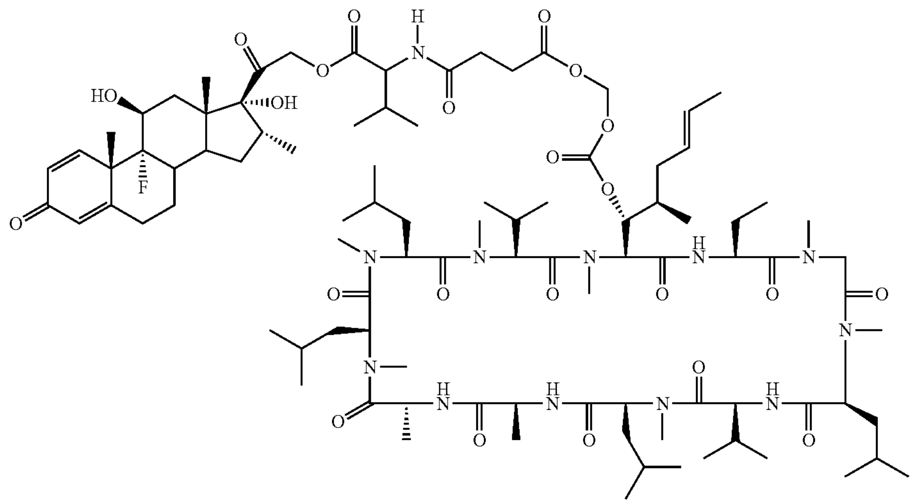 | 5.79 | 5.72 | 1872 MNa+ |
| 28 L68 | 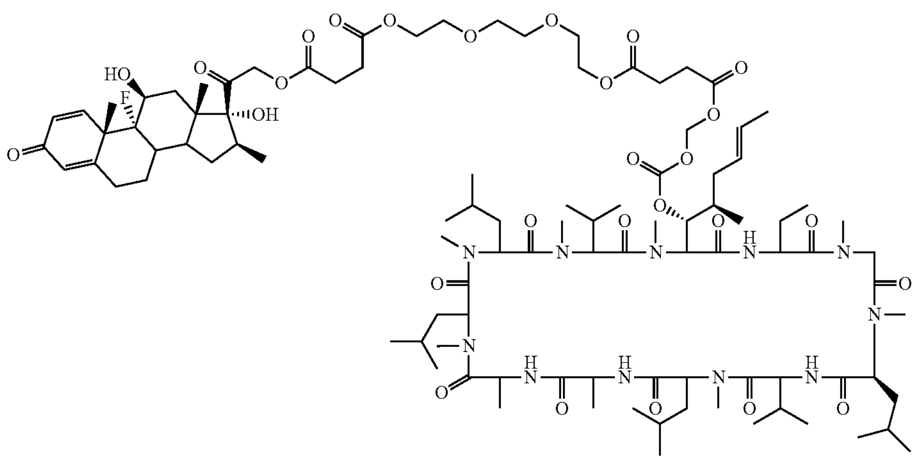 [SMILES: C/C=C/C[C@@H](C)[C@@H](OC(=O)OCOC(=O)CCC(=O)OCCOCCOCCOC(=O)CCC(=O)OCC(=O)[C@@]1(O)[C@@H](C)CC2C3CCC4=CC(=O)C=C[C@]4(C)[C@@]3(F)[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C] | 5.81 | 5.69 | 2006 MNa+ |
Dexamethasone reacted with one molecule of Cyclosporine A to form the following hybrid compounds as shown in Scheme 4 with the results described in Table 6.
Scheme 4
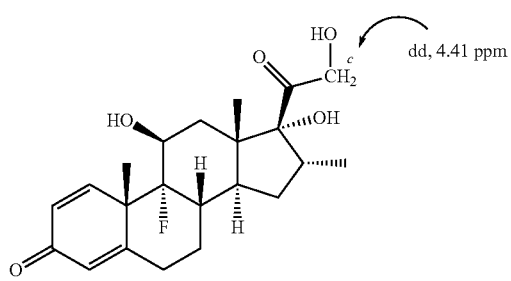
Dexmethasone -continued
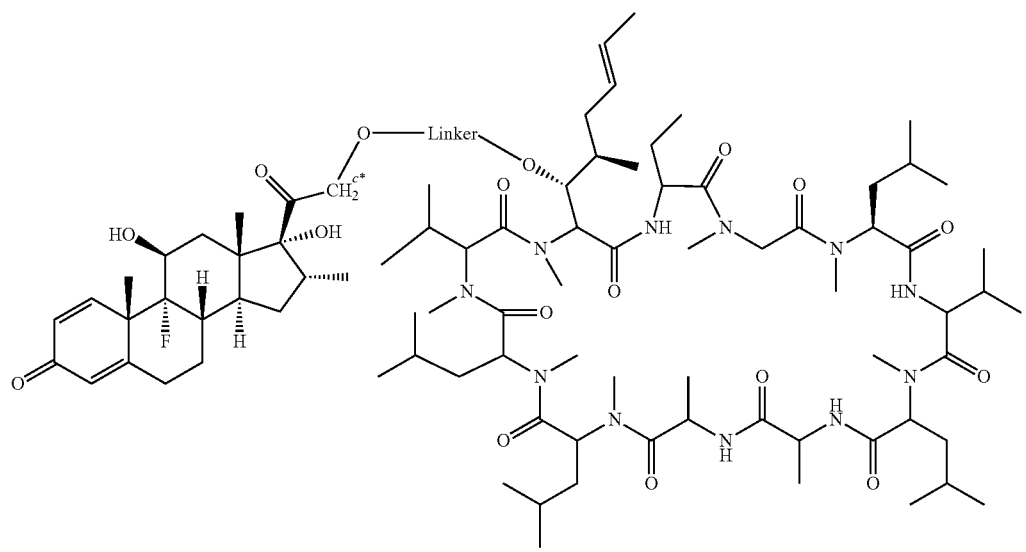
TABLE 6
| * Comp. Linker | Structure | Ha* δ (ppm) | Hb* δ (ppm) | Mass |
|---|---|---|---|---|
| 29 L63 | 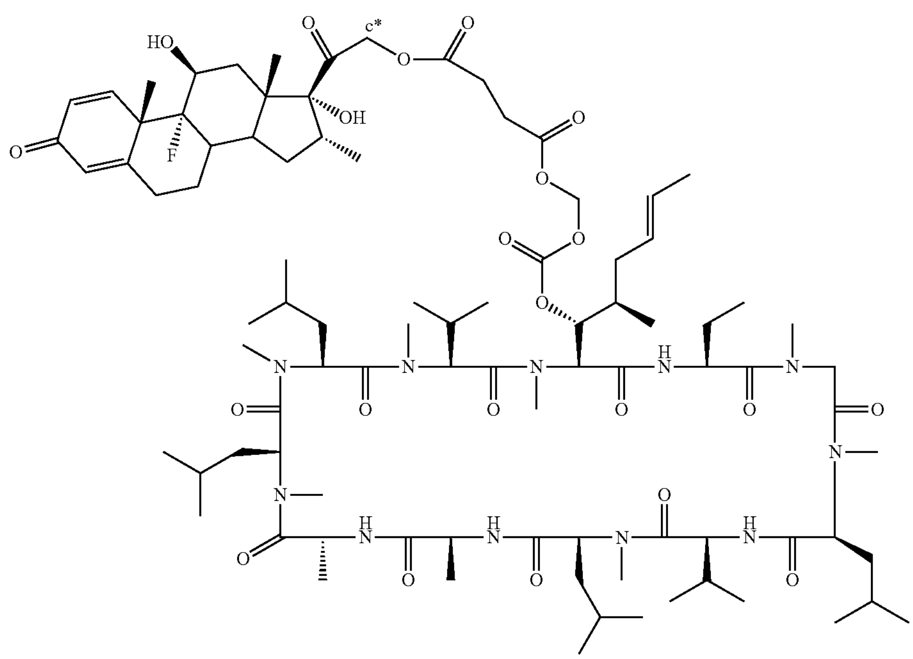 | 5.94 | 5.58 | 1773 MNa+ |

TABLE 6-continued

| * Comp. Linker | Structure | Ha* δ (ppm) | Hb* δ (ppm) | Mass |
|---|---|---|---|---|
| 30 L61 | 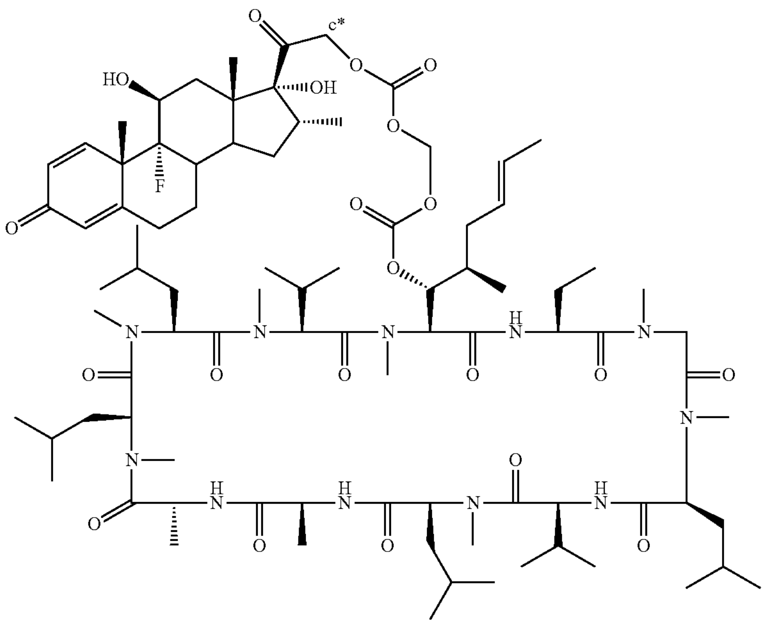 | | | |
| 31 L75 | 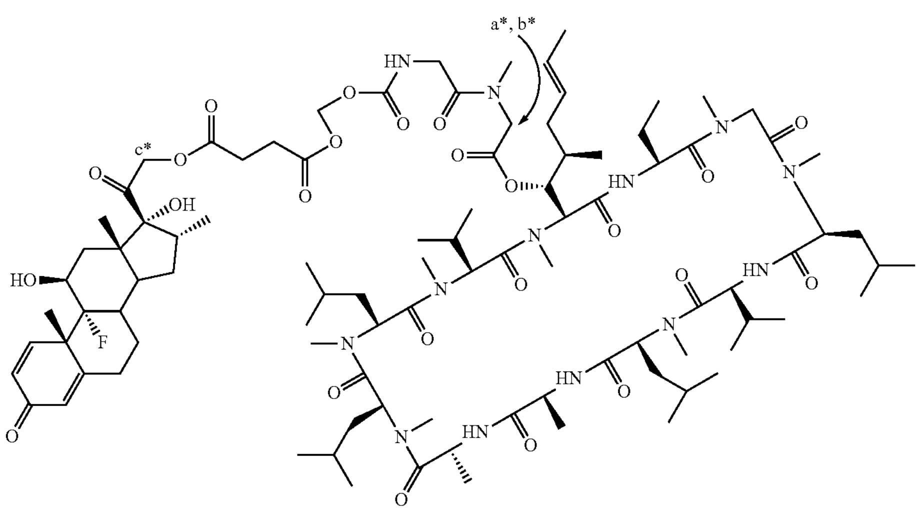 | 5.73 | | 1901 MNa+ |

TABLE 6-continued

| * Comp. Linker | Structure | Ha* δ (ppm) | Hb* δ (ppm) | Mass |
|---|---|---|---|---|
| 32 L68 | 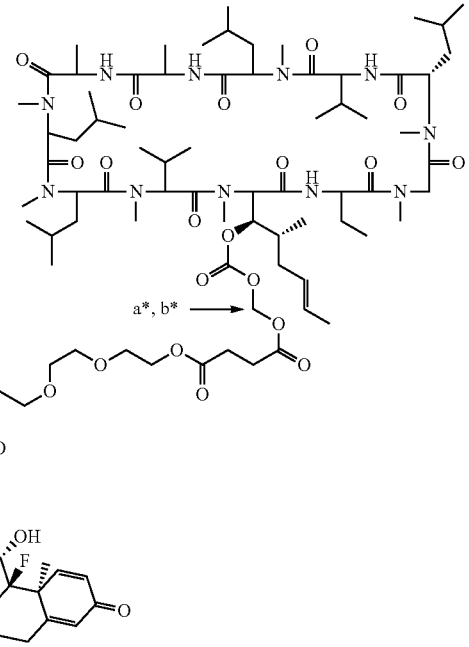 | 5.82 | 5.69 | 2005 MNa+ |
| 20 L69 | 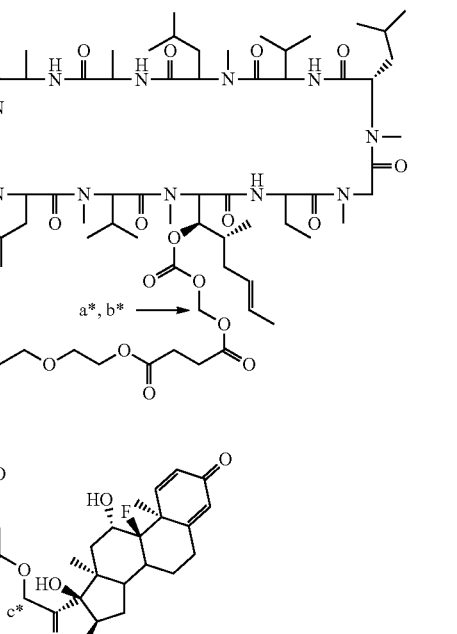 | 5.82 | 5.69 | 2050 MNa+ |

In Vitro Metabolic Stability in Human Recombinant Carboxylesterases

Human recombinant carboxylesterases were purchased from a commercial vendor (BD Gentest™, Bedford, Mass.). All metabolic stability experiments were performed in triplicate in 96-well plate format. The final incubation mixture contained 1 μM test compound and 0.1 mg/mL human recombinant carboxylesterase mixture in a final volume of 0.5 mL 0.1M potassium phosphate buffer (pH=6.0). The final percentage of solvent in the incubation was less than 1.0% to prevent inhibition of enzymatic activity. Following a pre-incubation at 37° C., test article was added to initiate the reaction. At designated time points (typically 120 minutes to capture the linear range of metabolite formation), 0.05 mL aliquots were removed from the incubation mixtures using a clean pipet tip and immediately placed in organic solvent to stop any esterase activity. The hydrolysis to the metabolites was confirmed to be due to esterase activity and not chemical lability.

The samples were analyzed by liquid chromatography with mass spectrometry (LC-MS/MS) detection to determine the metabolite concentrations resulting from the metabolism of the hybrid compounds. Internal standards were used to compensate for variability from sample processing, chromatographic elution, mass spectrometer response and ion suppression by matrix components.

Results

Table 7 Lists the rate of metabolite formation in human recombinant carboxylesterases.

TABLE 7

| Comp. No. | Rate of formation Metabolite 1 (nM/min/mg) | Rate of formation Metabolite 2 (nM/min/mg) |
|---|---|---|
| 5 | 84.4 ± 7.52 Prednisolone | 35.6 ± 0.63 Cyclosporine A |
| 6 | 30.4 ± 1.06 Prednisolone | 34.4 ± 3.85 Cyclosporine A |
| 7 | 4.26 ± 1.31 Prednisolone | 1.31 ± 0.18 Cyclosporine A |
| 32 | 20.4 ± 3.18 Dexamethasone | 13.4 ± 1.31 Cyclosporine A |
| 20 | 12.0 ± 0.88 Dexamethasone | 13.9 ± 1.11 Cyclosporine A |
| 21 | 20.0 ± 1.32 Prednisolone | 21.6 ± 0.03 Cyclosporine A |
| 22 | 38.4 ± 3.32 Prednisolone | 46.5 ± 3.16 Cyclosporine A |

The data demonstrate that linkage of cyclosporine A and a steroid (e.g. dexamethasone and prednisolone) as a single hybrid compound was hydrolyzed enzymatically in human recombinant carboxylesterases to their respective individual cyclosporine A and steroid drugs.

What is claimed is:

1. A hybrid drug comprising one cyclosporine A moiety and one steroid moiety, which are covalently connected via a linker, wherein the hybrid drug is selected from:

21-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 1-({[({(2R,4E)-1-[(2S,11S,20S,26R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(3R)-3-amino-4,18-dioxo-5,8,11,14,17-pentaoxahenicosane-1,21-dioate;

6-[(6-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-6-oxohexyl)oxy]-6-oxohexyl {[({(2R,4E)-1-[(11S,17R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate;

8-[(4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-4-oxobutanoyl)oxy]octyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl (2E,5R)-6-[(11S,17R,26R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-5-methyl-8,12,19-trioxo-7,9,11,18-tetraoxatetracos-2-en-24-yl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl 6-({[({(2R,4E)-1-[(2S,11 S,17R,23 S,26R,32R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-6-oxohexyl rel-butanedioate;

2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-(14R,16E)-13-[(2R,5R,11S,17R,29S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-14-methyl-4,7,11-trioxo-2-(propan-2-yl)-8,10,12-trioxa-3-azaoctadec-16-en-1-oate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(14R,16E)-13-[(2R,5R,11 S,17R,29R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-14-methyl-4,7,11-trioxo-2-(propan-2-yl)-8,10,12-trioxa-3-azaoctadec-16-en-1-oate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,21-dioxo-5,8,11,14,17,20-hexaoxatetracosane-1,24-dioate;

2-{2-[(4-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}-4-oxobutanoyl)oxy]ethoxy}ethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate;

{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16S,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,15-dioxo-5,8,11,14-tetraoxaoctadecane-1,18-dioate;

rel-(2R)-4-({[({(2S,4E)-1-[(11R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-2-[(4-{2-[(9S,10R,11R,13R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethoxy}-4-oxobutanoyl)amino]-4-oxobutanoic acid;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(10R,18R,20E)-10-amino-17-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-18-methyl-4,11,15-trioxo-12,14,16-trioxa-5-azadocos-20-en-1-oate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-benzene-1,4-dicarboxylate;

1-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 4-({[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(2R)-2-aminobutanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-(2E)-but-2-enedioate;

{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16S,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,18-dioxo-5,8,11,14,17-pentaoxahenicosane-1,21-dioate;

{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,18-dioxo-5,8,11,14,17-pentaoxahenicosane-1,21-dioate;

{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-4,15-dioxo-5,8,11,14-tetraoxaoctadecane-1,18-dioate;

4-{2-[(10R,11 S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 1-({[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl) rel-(2S)-2-aminobutanedioate;

(2R)-2-amino-3-({[({(2R,4E)-1-[(5R,11 S,26R)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methoxy)-3-oxopropyl 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl 1-{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}ethyl rel-4,15-dioxo-5,8,11,14-tetraoxaoctadecane-1,18-dioate;

1-{(2R,4E)-1-[(2S,5R,11 S,14S,17R,20S,23R,26R,29S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl} 14-{2-[(9R,10 S,11 S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl}rel-3-methyl-4,7,11-trioxo-8,10-dioxa-3,6-diazatetradecane-1,14-dioate;

14-{2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl} 1-{(2R,4E)-1-[(11S,23 S,26S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}rel-3-methyl-4,7,11-trioxo-8,10-dioxa-3,6-diazatetradecane-1,14-dioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,18-dioxo-5,8,11,14,17-pentaoxahenicosane-1,21-dioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-4,15-dioxo-5,8,11,14-tetraoxaoctadecane-1,18-dioate;

(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-2,2'-oxydiacetate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(12R,14E)-11-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-12-methyl-5,9-dioxo-3,6,8,10-tetraoxahexadec-14-en-1-oate;

{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-butanedioate;

{[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl 2-[(9R,10S,11S,13S,16S,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-butanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-pentanedioate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl {[({(2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl}oxy)carbonyl]oxy}methyl rel-butanedioate; and 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl (2R,4E)-1-[(11S)-5-ethyl-1,7,10,16,20,23,25,28,31-nonamethyl-11,17,26,29-tetrakis(2-methylpropyl)-3,6,9,12,15,18,21,24,27,30,33-undecaoxo-14,32-di(propan-2-yl)-1,4,7,10,13,16,19,22,25,28,31-undecaazacyclotritriacontan-2-yl]-2-methylhex-4-en-1-yl rel-2,2'-oxydiacetate;

and pharmaceutically acceptable salts thereof.

2. A hybrid drug comprising one cyclosporine A moiety and one steroid moiety, which are covalently connected via a linker, wherein the hybrid drug is selected from:

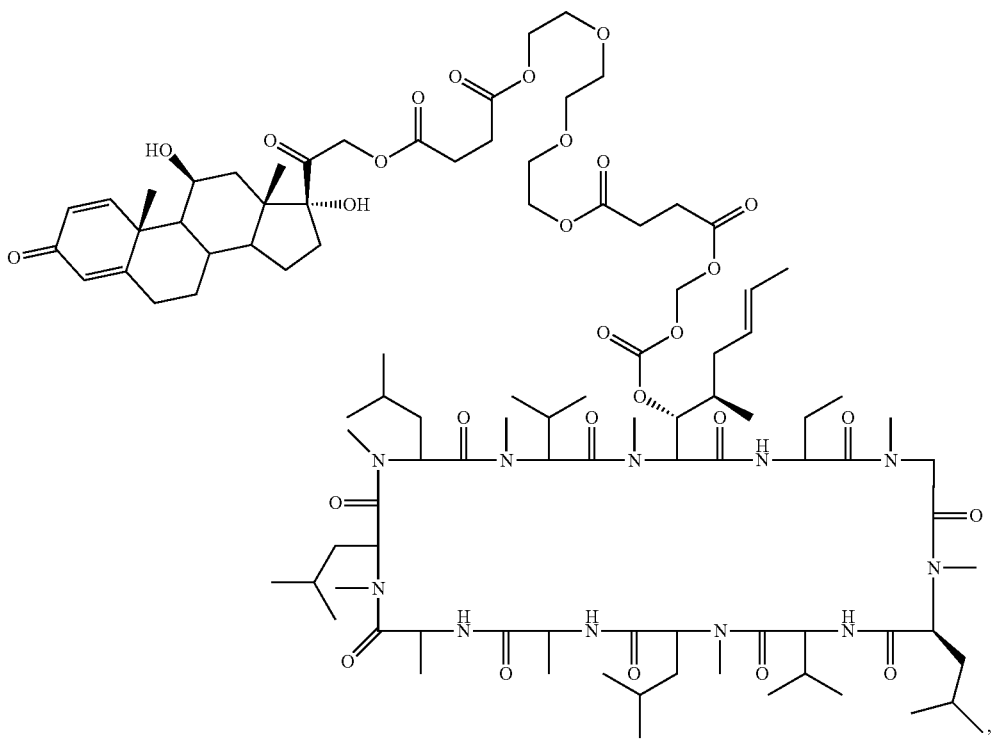

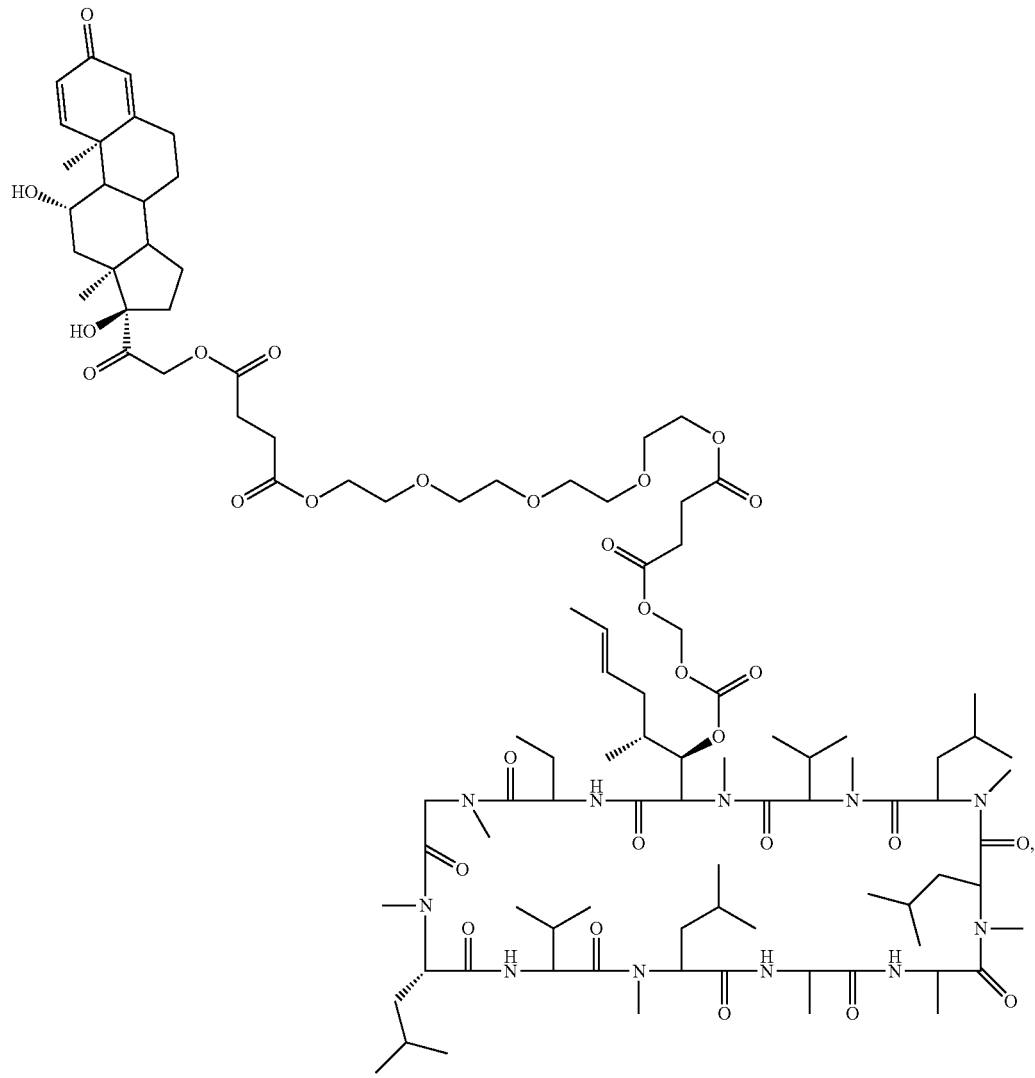

-continued
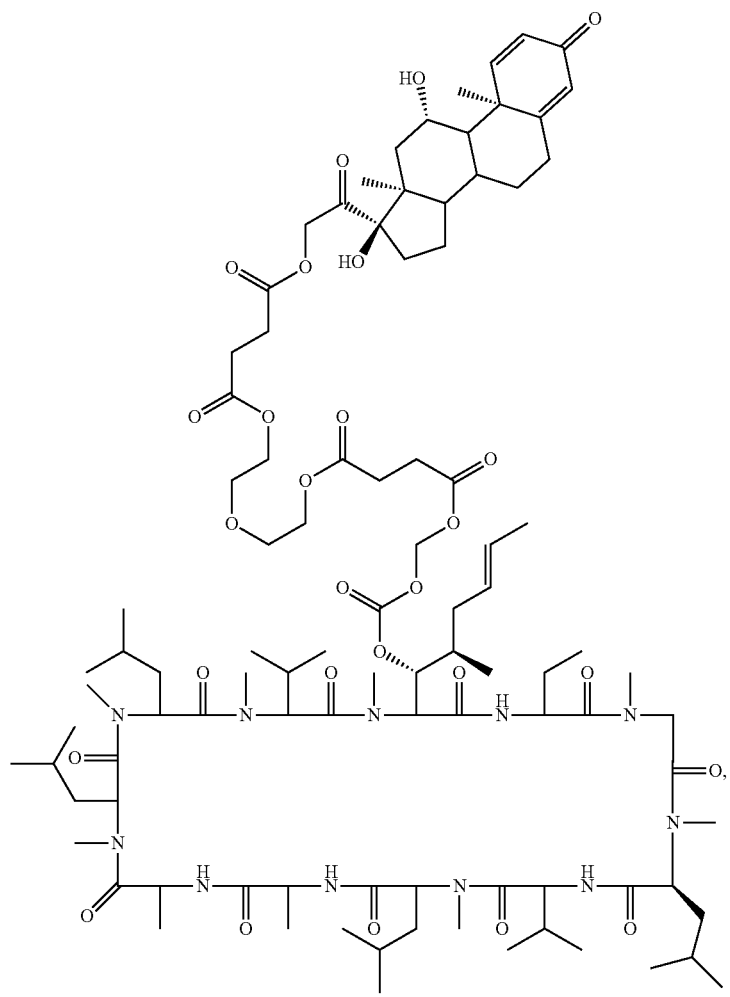
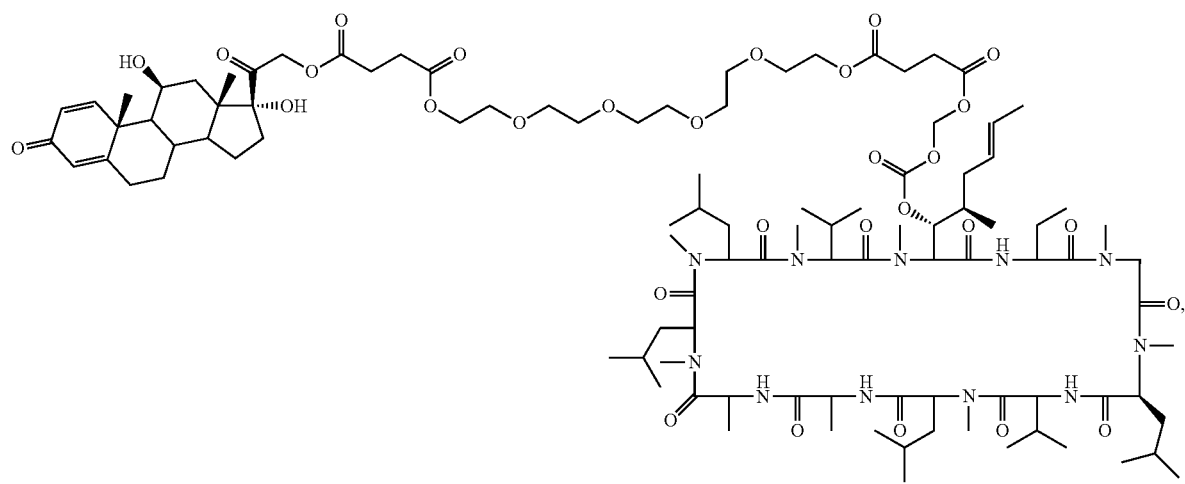

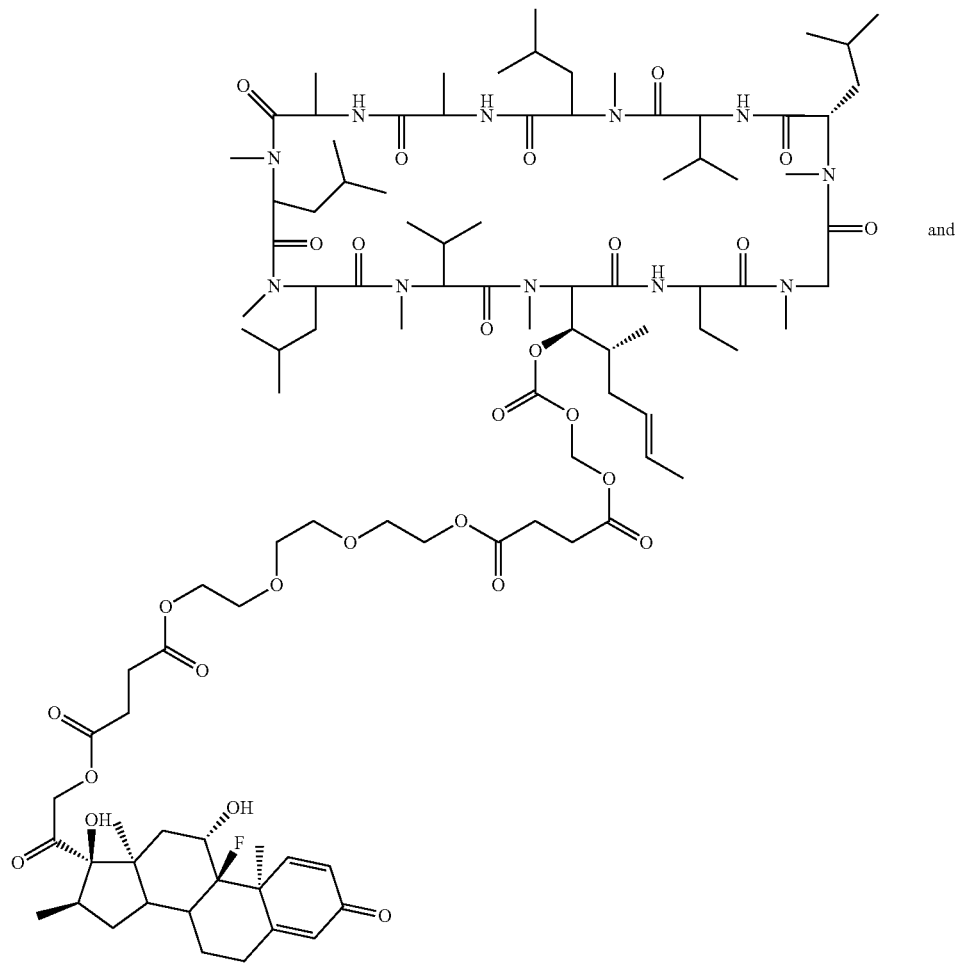 [SMILES: C/C=C/C[C@@H](C)[C@@H](OC(=O)OCOC(=O)CCC(=O)OCCOCCOCCOC(=O)CCC(=O)OCC(=O)[C@@]1(O)[C@H](C)CC2C3CCC4=CC(=O)C=C[C@]4(C)[C@@]3(F)[C@@H](O)C[C@@]21C)C1C(=O)NC(CC)C(=O)N(C)CC(=O)N(C)[C@@H](CC(C)C)C(=O)NC(C(C)C)C(=O)N(C)C(CC(C)C)C(=O)NC(C)C(=O)NC(C)C(=O)N(C)C(CC(C)C)C(=O)N(C)C(CC(C)C)C(=O)N(C)C(C(C)C)C(=O)N1C ; "and"] and

-continued
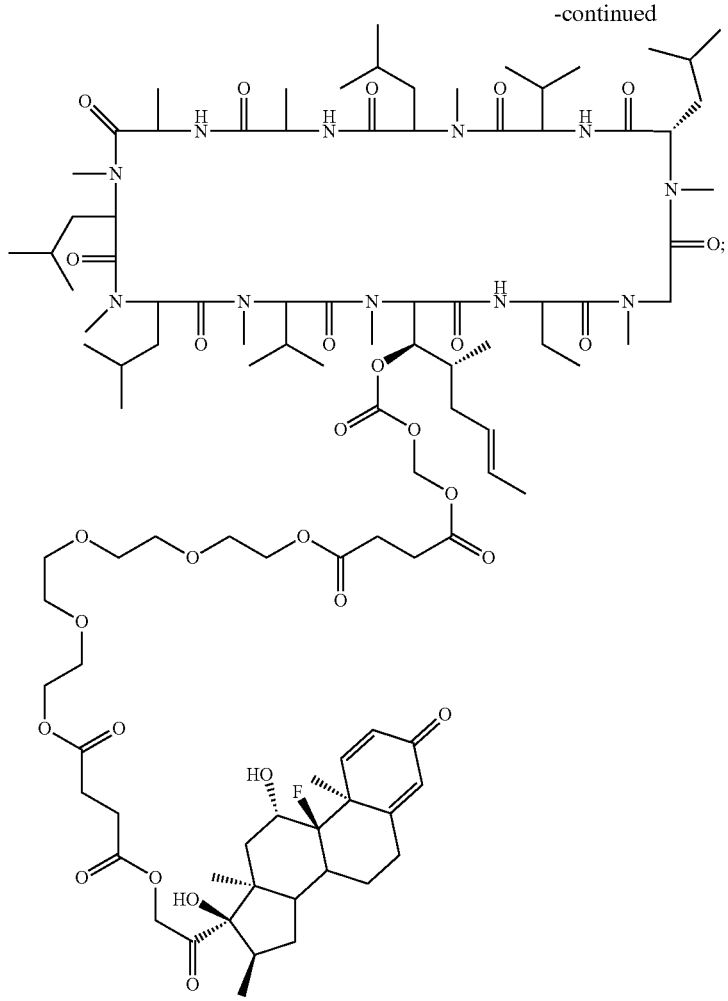
and pharmaceutically acceptable salts thereof.
* * * * *